(12) United States Patent
Wiesman et al.

(10) Patent No.: US 11,189,363 B2
(45) Date of Patent: Nov. 30, 2021

(54) GENERATION OF NUCLEAR MAGNETIC RESONANCE MULTIDIMENSIONAL T1(SPIN-MATRIX)-T2(SPIN-SPIN) ENERGY RELAXATION MAPS AND USES THEREOF

(71) Applicants: Ze'ev Wiesman, Lehavim (IL); Charles Linder, Rehovot (IL); Ofer Levi, Lehavim (IL)

(72) Inventors: Ze'ev Wiesman, Lehavim (IL); Charles Linder, Rehovot (IL); Ofer Levi, Lehavim (IL); Michael Saunders, Palo Alto, CA (US)

( * ) Notice: Subject to any disclaimer, the term of this patent is extended or adjusted under 35 U.S.C. 154(b) by 3 days.

(21) Appl. No.: 16/562,847

(22) Filed: Sep. 6, 2019

(65) Prior Publication Data

US 2020/0241095 A1  Jul. 30, 2020

Related U.S. Application Data

(63) Continuation of application No. PCT/IL2018/050279, filed on Mar. 9, 2018.
(Continued)

(51) Int. Cl.
*G16C 20/20* (2019.01)
*G01N 24/08* (2006.01)
(Continued)

(52) U.S. Cl.
CPC ............ *G16C 20/20* (2019.02); *G01N 24/08* (2013.01); *G01N 24/081* (2013.01);
(Continued)

(58) Field of Classification Search
CPC .... G01N 24/08; G01N 24/081; G01R 33/307; G01R 33/448; G01R 33/4625; G01R 33/465; G01R 33/50; G01V 3/32
See application file for complete search history.

(56) References Cited

U.S. PATENT DOCUMENTS 7,388,374 B2    6/2008  Minh et al.
9,222,902 B2 *  12/2015  Gruber ................ G01R 33/448
(Continued)

FOREIGN PATENT DOCUMENTS

CN     106199474    12/2016

OTHER PUBLICATIONS

V. Bortoltti, R. J. S. Brown., P. Fantazzini, G. Landi, F. Zama (2016): Uniform penalty inversion of two-dimensional NMR relaxation data, Inverse Problems 33(1).
(Continued)

*Primary Examiner* — Dixomara Vargas
(74) *Attorney, Agent, or Firm* — Nixon & Vanderhye P.C.

(57) ABSTRACT

A method of characterizing chemical and/or morphological features of a material, comprising acquiring energy relaxation data from 1H low field nuclear magnetic resonance ($^1$H LF-NMR) measurements of said material, converting the relaxation signals into a multidimensional distribution of longitudinal and transverse relaxation times by solving an inverse problem under both $L_1$ and $L_2$ regularizations and further imposing a non-negativity constraint, and identifying one or more characteristics of said material with the aid of said multidimensional T1-T2 distribution. The method is useful, inter alia, in monitoring chemical processes, screening of additives and quality control.

26 Claims, 16 Drawing Sheets

Related U.S. Application Data

(60) Provisional application No. 62/468,954, filed on Mar. 9, 2017.

(51) Int. Cl.
 *G01R 33/30* (2006.01)
 *G01R 33/44* (2006.01)
 *G01R 33/46* (2006.01)
 *G01R 33/465* (2006.01)
 *G01R 33/50* (2006.01)
 *G01V 3/32* (2006.01)

(52) U.S. Cl.
 CPC ......... *G01R 33/307* (2013.01); *G01R 33/448* (2013.01); *G01R 33/465* (2013.01); *G01R 33/4625* (2013.01); *G01R 33/50* (2013.01); *G01V 3/32* (2013.01)

(56) References Cited

U.S. PATENT DOCUMENTS

| | | | | |
|---|---|---|---|---|
| 10,393,839 | B2* | 8/2019 | Altbach | G01R 33/54 |
| 10,466,186 | B2* | 11/2019 | Kadayam Viswanathan | G01R 33/448 |
| 10,782,373 | B2* | 9/2020 | Altbach | G16H 30/40 |
| 2010/0259258 | A1* | 10/2010 | Fransson | G01R 33/5617 |
| | | | | 324/303 |
| 2013/0002246 | A1* | 1/2013 | Venkataramanan | G01R 33/448 |
| | | | | 324/303 |
| 2013/0179083 | A1* | 7/2013 | Gruber | G01R 33/448 |
| | | | | 702/13 |
| 2013/0181711 | A1* | 7/2013 | Chaari | G01R 33/5611 |
| | | | | 324/309 |
| 2013/0261979 | A1* | 10/2013 | Al-Muthana | G01V 3/38 |
| | | | | 702/12 |
| 2014/0114576 | A1* | 4/2014 | Jain | G01V 11/00 |
| | | | | 702/7 |
| 2014/0212901 | A1 | 7/2014 | Lowery, Jr. et al. | |
| 2014/0285190 | A1* | 9/2014 | Allen | G01N 24/081 |
| | | | | 324/303 |
| 2015/0006114 | A1* | 1/2015 | Altbach | G01R 33/54 |
| | | | | 702/189 |
| 2015/0015250 | A1* | 1/2015 | Gzara | G01N 24/08 |
| | | | | 324/303 |
| 2015/0130460 | A1* | 5/2015 | Valori | G01N 24/081 |
| | | | | 324/309 |
| 2015/0130463 | A1 | 5/2015 | Wellman et al. | |
| 2015/0145513 | A1* | 5/2015 | Li | G01V 3/32 |
| | | | | 324/303 |
| 2015/0177351 | A1* | 6/2015 | Venkataramanan | G01R 33/448 |
| | | | | 324/309 |
| 2015/0308970 | A1* | 10/2015 | Massefski, Jr. | G01N 24/088 |
| | | | | 435/13 |
| 2016/0018421 | A1* | 1/2016 | Lowery, Jr. | A61B 5/02007 |
| | | | | 435/13 |
| 2016/0139291 | A1* | 5/2016 | Saidian | G01N 24/081 |
| | | | | 324/303 |
| 2016/0170065 | A1* | 6/2016 | Jain | G01V 3/14 |
| | | | | 324/303 |
| 2016/0341680 | A1* | 11/2016 | Kadayam Viswanathan | G01N 24/081 |
| 2017/0003412 | A1* | 1/2017 | Bordakov | G01V 3/32 |
| 2019/0353733 | A1* | 11/2019 | Altbach | G01R 33/54 |
| 2019/0353823 | A1* | 11/2019 | Anand | G01R 33/4633 |

OTHER PUBLICATIONS

Berman, P., Levi, O., Parmat, Y., Saunders, M. and Wiesman, Z. (2013): Laplace Inversion of LR-NMR Relaxometry Data using Sparse Representation Methods, Concepts in Magnetic Resonance A, 42, p. 72-88.

Meiri, N, Berman, P., Colnago, L.A, Moraes, T.B., Linder, C. and Wiesman, Z. (2015): Liquid phase characterization of molecular interactions in polyunsaturated and n-fatty acid methyl esters by 1H Low field nuclear magnetic resonance, Biotechnology for Biofuels 8, p. 96.

International Search Report for PCT/IL2018/050279 dated Jun. 19, 2018, 6 pages.

Written Opinion of the ISA for PCT/IL2018/050279 dated Jun. 19, 2018, 9 pages.

Kovrlija et al., "Hydrothermal changes in wheat starch monitored by two-dimensional NMR", Food Chemistry, vol. 214, 2017, pp. 412-422.

Berman et al., "Novel $^1$H low field nuclear magnetic resonance applications for the field of biodiesel", Biotechnology for Biofuels, 6:55, 2013, pp. 1-20.

Gómez et al., "Digestion of cattle manure under mesophilic and thermophilic conditions: characterization of organic matter applying thermal analysis and $^1$H NMR", Biodegradation, vol. 22, No. 3, 2011, pp. 623-635.

Carneiro et al., Quality Attributes in Shrimp Treated with Polyphosphate after Thawing and Cooking: A Study using Physicochemical Analytical Methods and Low-Field $^1$H NMR, J. Food Process Eng., vol. 36, bo 4, Jan. 28, 2013, pp. 492-499.

Hills et al., "$T_1$-$T_2$ Correlation Analysis of Complex Foods", Appl. Magn. Reson., vol. 26, No. 4, 2004, pp. 543-560.

Marigheto et al., "Two-dimensional NMR relaxation studies of apple quality", Postharvest Biology and Technology, vol. 48, No. 3, 2008, pp. 331-340.

Berman et al., "$^1$H low field nuclear magnetic resonance relaxometry for probing biodiesel autoxidation" Fuel, vol. 177, 2016, pp. 315-325.

\* cited by examiner

GENERATION OF NUCLEAR MAGNETIC RESONANCE MULTIDIMENSIONAL T1(SPIN-MATRIX)-T2(SPIN-SPIN) ENERGY RELAXATION MAPS AND USES THEREOF

This application is a continuation of International Application No. PCT/IL2018/050279 filed Mar. 9, 2018, which designated the U.S. and claims benefit to U.S. Provisional Application No. 62/468,954 filed Mar. 9, 2017, the entire contents of each of which are hereby incorporated by reference.

Nuclear magnetic resonance (NMR) is a spectroscopic technique used primarily to elucidate the structure of organic compounds and porous structures of water-containing inorganics and ceramics.

Data collected by NMR measurements can be presented in the form of multi-dimensional maps. Such maps provide an easy-to-understand format. See, for example, U.S. Pat. No. 7,388,374, which describes interpretation methods for NMR maps based on measurements taken on a fluid sample from a borehole.

Data acquired by NMR measurements includes spin-lattice/matrix energy relaxation time (T1) and spin-spin energy relaxation time (T2). Relaxation processes permit the population of nuclear spins to return to equilibrium after absorption of the radio frequency energy delivered by the NMR instrument, either through a mechanism of spin-lattice interactions (the lattice/matrix is the environment around the nucleus, namely, neighboring atoms or molecules) or the mechanism of spin-spin interactions. That is, T1 and T2 are the time constants associated with exponential decay of the magnetization vector until it reaches its equilibrium value: T1 indicates how fast the magnetization relaxes back along the z-axis (so it is called longitudinal relaxation time), and T2 measures how fast the spins exchange energy in the transverse (xy) plane (so it is called transverse relaxation time).

1-D analysis of either spin-lattice or spin-spin energy relaxation times, that is, conversion of low-resolution NMR relaxation signals into a continuous distribution of either T1 or T2 to give a graph of different peaks as a function of T1 or T2 was demonstrated [Berman, P. Leshem, A., Etziony, O., Levi, O, Parmat, Y, Saunders, M and Wiesman, Z. (2013): Novel $^1$H Low Resolution (LR)-NMR Applications for the Biodiesel Industry, Biotechnology for Biofuels 6: p. 55; and also Berman, P., Levi, O., Parmat, Y., Saunders, M. and Wiesman, Z. (2013): Laplace Inversion of LR-NMR Relaxometry Data using Sparse Representation Methods, Concepts in Magnetic Resonance A. 42, p. 72-88]. Other publications worth mentioning are based on T2 relaxation time maps [see Meiri, N, Berman, P., Colnago, L. A, Moraes, T. B., Linder, C. and Wiesman, Z. (2015): Liquid phase characterization of molecular interactions in polyunsaturated and n-fatty acid methyl esters by 1H Low field nuclear magnetic resonance, Biotechnology for Biofuels 8, p. 96; and Berman, P., Meiri, N., Linder, C., Wiesman Z. (2016): 1H Low field nuclear magnetic resonance relaxometry for probing biodiesel autoxidation, Fuel 177, p. 315-325].

Uniform penalty inversion of two-dimensional NMR relaxation data based on Tikhonov-like regularization was also reported [V. Bortoltti, R. J. S. Brown., P. Fantazzini, G. Landi, F. Zama (2016): Uniform penalty inversion of two-dimensional NMR relaxation data, Inverse Problems 33(1)]. Another method is described in US 2016/0170065, where T1-T2 maps are generated to characterize geological formations such as water saturation and permeability.

The approach based on 1D T1 or T2 relaxation time maps, or current state of the art T1 vs. T2 graphical maps, or other approaches such as solid state NMR ($^{13}$C CP/MAS NMR), FTIR, XRD, thermal gravimetric analysis (TGA) and scanning microscopy (SEM), cannot give an accurate and efficient peak-resolved morphological and chemical map of different domains within complex chemical and/or complex morphological mixtures based on different energy interaction strengths between the different components as affected by micro, nano molecular morphologies and the chemical environment around the different morphologies. If this were possible it would have many applications in different areas such as biological systems, as for example but not limited to biological membrane stability, and industries such as, but not limited to, fuel, biodiesel, food, cosmetics and pharmaceuticals, etc.

To accomplish complex morphological and chemical domain analysis with the aid of multidimensional T1-T2 maps, improved signal processing and computational methods of relaxation signals are required. As shown in detail below, the conversion of relaxation signal into a continuous distribution of relaxation components is an ill-posed inverse Laplace transform problem. The approach to solving such a problem consists of representing it in a discrete matrix form and computing the distribution matrix from a minimization problem, applying one or more regularization strategies. We have now found that by using both $L_1$-regularization (which increases the sparsity of the distribution matrix) together with $L_2$-regularization and a non-negativity constraint, and carefully choosing the regularization parameters in the minimization problem (also known as "penalty weights" assigned to the $L_1$ and $L_2$ norms), it is possible to solve the problem effectively and generate useful T1-T2 maps with enhanced peak resolution. Determining appropriate values for the $L_1$ and $L_2$ weights is significant for obtaining good and accurate solution for the reconstruction problem. We have found that the penalty weights are affected by several factors such as the size of problem input and output, the SNR (signal to noise) level of the measurements as well as the signal intensity. The choice of L1 allows for peak sharpness and L2 for smoothness and reduction in noise peaks, such that the respective L1 and L2 values should be optimally balanced for achieving the well resolved distribution of peaks representing the chemical and morphological domains of the materials.

Accordingly, one aspect of the present invention is a method for characterizing chemical and morphological features of a material, especially a complex mixture composed of multiple materials or phases that is about to undergo or is undergoing a chemical or a morphological change. For example, a starting material that is about to be converted into a useful end product may be analyzed by the method of invention to predict the outcome of the contemplated conversion, and/or to carry out a preconditioning process or addition of components to enhance the conversion. Processes may be monitored by periodically generating T1-T2 based multidimensional maps to allow personnel such as engineers and production managers to determine if the process under consideration advances at an acceptable rate or is about to cease due to exhaustion or decreased accessibility of active phases and optimize the process accordingly, in order to increase yield. The method may be used for screening reagents, to determine their suitability for advancing/suppressing chemical reactions involving complex materials.

The invention provides a method of characterizing chemical and/or morphological features of a material, comprising acquiring energy relaxation data from NMR measurements of said material, converting the relaxation signals into a multidimensional distribution of longitudinal and transverse relaxation times by solving an inverse problem under both $L_1$ and L2 regularizations and further imposing a non-negativity constraint, and identifying one or more characteristics of said material with the aid of said multidimensional T1-T2 distribution (e.g., position and intensity of peaks, T1/T2 ratios, as illustrated below).

It should be noted that the respective regularization parameters $\lambda_1$ and $\lambda 2$ are preferably set according to the signal-to-noise level of said measurements, signal intensity, dimensions of the acquired set of data and dimensions of an input matrix of distribution components of interest.

More specifically, the invention provides a method of characterizing chemical and/or morphological features of a material, comprising the following steps:

i) acquiring relaxation data from NMR measurements;

ii) computing multidimensional T1-T2 distribution by solving the following minimization problem:

$$\min_{f,c,r} \lambda_1 \|c\|_1 + \frac{1}{2}\lambda_2 \|c\|_2^2 + \frac{1}{2}\|r\|_2^2 \quad (1)$$

$$\text{s.t.} \quad K_1 F K_2 + R = S,$$

$$-f + Bc = 0, f \geq 0,$$

wherein (s.t. means "subject to"):

S is $ns_1 \times ns_2$ matrix with the measured relaxation data;

F is $nf_1 \times nf_2$ matrix of unknown distribution components, and f=vec(F) is a vector with length of $nf_1 \times nf_2$ containing the elements of the matrix F concatenated by columns;

$K_1$ and $K_2$ and are Laplace operators, that is, matrices of sizes $ns1 \times nf1$ and $ns2 \times nf2$, respectively, and their elements are defined as follows:

$$K_1(i, j) = 1 - 2\exp\left(-\frac{t_1(i)}{T_1(j)}\right), i = 1, \ldots, ns_1 \; j = 1, \ldots, nf_1$$

$$K_2(i, j) = \exp\left(-\frac{t_2(i)}{T_2(j)}\right), i = 1, \ldots, nf_2 \; j = 1, \ldots, ns_2$$

R is a matrix of residuals, and r=vec(R) is a vector of the elements of the matrix R concatenated by columns;

B is a dictionary matrix, c is a representation of the solution f by the B dictionary, and wherein the problem is solved with a penalty function comprising $L_1$ regularization term $\lambda_1 \|c\|_1$ (that is, a sparsity-inducing regularization) and $L_2$ regularization term $\lambda_2 \|c\|_2^2$, where $\lambda_1$ and $\lambda_2$ are the $L_1$ and $L_2$ regularization parameters, respectively, and further with a non-negativity constraint imposed on the solution. $\lambda 1$ and $\lambda 2$ are preferably calculated by the following formulas:

$$\lambda_1 = C_1 \times SMX \times \frac{ns_1 \times ns_2}{nf_1 \times nf_2 \times SNR}$$

$$\lambda_2 = C_2 \times SMX \times \frac{ns_1^2 \times ns_2^2}{nf_1^2 \times nf_2^2 \times SNR}$$

wherein:

$C_1$ is from 0.1 to 0.5 (preferably from 0.2 to 0.4, more preferably from 0.25 to 0.35, for example, about 0.3);

$C_2$ is from 0.0003 to 0.0007 (preferably from 0.0004 to 0.0006, more preferably about 0.0005);

SMX is the maximal magnitude of the relaxation signal array after light smoothing; and SNR is the signal to noise ratio of the measured relaxation coefficients;

iii) optionally displaying said distribution in the form of a multidimensional map having at least T1 relaxation axis and T2 relaxation axis; and iv) assigning one or more peaks identified on said spectrum to a chemical and morphological feature of said material.

Regarding step (i), that is, to acquire NMR relaxation data, NMR measurements may be carried out in a laboratory on a sample removed from a starting material of interest or on a sample removed from a reaction mass when a chemical process is in progress, using, e.g., standard, lab top in size, commercially available LF H1 NMR instruments, easily used on site or off site as required. The method may also be applied on-line for continuous monitoring without sample removal. The samples may be analyzed with or without minor modification. As for a non limiting example, water is added to the sample so that water's $^1$H which is used to generate $T_1$ and $T_2$ energy relaxation signals as modified by the chemical morphological structure of the material substrate to which it is added. The sample may be discarded or added back to the source from which it was taken. Different techniques may be utilized to measure $T_1$ and $T_2$, based on the application of different pulse sequences. T1 is conventionally measured by employing inversion recovery sequence [180–$t_1$]. Determination of T2 is achieved by using the Carr Purcell Meiboom Gill (CPMG) pulse sequence, initiated by 90° pulse followed by a series of 180° C. pulses. For the 2D measurements, the inversion recovery step [180°–$t_1$] is inserted prior to the CPMG sequence. The instrument-generated output consists of the aforementioned S matrix, a 2D set of sampled relaxation times. That is, an array with ns1 rows and ns2 columns corresponding to the elements of the two time series of sampling points.

Regarding step (ii), that is, the computation of a two-dimensional T1-T2 distribution by solving the minimization problem (1), it should be noted that the relation between the 2D continuous relaxation signal, $s(t_1,t_2)$, and the 2D continuous spectrum distribution, $f(T_1,T_2)$, is given by the following equation:

$$s(t_1, t_2) = \int_0^\infty \int_0^\infty (1 - e^{-t_1/T_1})e^{-t_2/T_2} f(T_1, T_2) dT_1 dT_2 + r(t_1, t_2) \quad (2)$$

As mentioned above, the measured relaxation signal is sampled at a discrete series of time points of length $ns_1$ $t_1(1), \ldots, t_1(ns_1)$ with respect to $t_1$ and length $ns_2$ $t_2(1), \ldots, t_2(ns_2)$ with respect to $t_2$.

In order to compute the 2D spectrum f in Eq. 2, it is necessary to discretize the continuous spectrum f and evaluate it in a 2D discrete set of $T_1$ and $T_2$ values. The sampling points are denoted by $T_1(1), \ldots, T_1(nf_1)$ for $T_1$ and $T_2(1), \ldots, T_2(nf_2)$ for $T_2$; and we denote by F the $nf_1$ by $nf_2$ 2D array of the unknown 2D spectrum.

In order to solve Eq. 2, the integral operator, which operates on the continuous spectrum function f, is discretized into two linear matrix operators that operate on the array F. Hence, the discrete form of Eq. 2 is $K_1 F K_2 + R = S$, where R is a 2D residuals array of the same dimensions as S.

As mentioned above, $K_1$ and $K_2$ are of sizes $ns_1 \times nf_1$ and $ns_2 \times nf_2$, respectively, and their elements are defined as follows:

$$K_1(i, j) = 1 - 2\exp\left(-\frac{t_1(i)}{T_1(j)}\right), i = 1, \ldots, ns_1 \; j = 1, \ldots, nf_1$$

$$K_2(i, j) = \exp\left(-\frac{t_2(i)}{T_2(j)}\right), i = 1, \ldots, nf_2 \; j = 1, \ldots, ns_2$$

It should be pointed out that not all double integrals operators can be discretized into a multiplication of the matrices from the left and the right on the 2D array of input argument. It is possible only when the double integral has the separability property, which is the case for the integral in Eq. 2.

In order to define $K_1$ and $K_2$ and determine their elements, the series of sampling points need to be defined.

$t_1(1), \ldots, t_1(ns_1)$ and $t_2(1), \ldots, t_2(ns_2)$ are determined by the sampling protocol of the NMR machine. They might be either uniformly sampled or exponentially sampled. Typical ranges, but not limited to, of the $t_1$ and $t_2$ values are between 0.0002 and 4 ms and the typical numbers of sampling points are 100 to 4000 for $t_1$ ($ns_1$) and 50 to 2000 for $t_2$ ($ns_2$).

Typical ranges, but not limited to, of the $T_1$ and $T_2$ values are between 0.0001 and 8 ms and need to be adjusted to the $t_1$ and $t_2$ sampling range. The typical number of sampling points are 100 to 2000 for $T_1$ ($nf_1$) and 30 to 1000 for $T_2$ ($nf_2$).

A significant improvement of the computational method of this invention resides in setting appropriate weights to the $L_1$-regularization and $L_2$-regularization. That is, choosing $\lambda_1$ and $\lambda_2$ efficiently. It is seen that the exact form of the formulas for $\lambda_1$ and $\lambda_2$ take into account the signal intensity, signal noise level, input and output arrays dimensions. The values of the coefficients $C_1$ and $C_2$ were shown to provide a robust and effective choice for a variety of lab NMR experiments that were carried out by the inventors. This guarantees that the same approach can be used for different machines and settings with no need for parameter tuning, which can be a long and tedious process.

It is seen that in order to determine $\lambda_1$ and $\lambda_2$, SMX (the maximal magnitude of the relaxation signal array after light smoothing) and SNR (the signal to noise ratio of the measured relaxation coefficients) are needed.

SMX can be computed by the following procedure:
1. Let s=vec(s) be a vector with length ns (ns is the product of ns1 and ns2), containing the elements of the matrix S arranged by columns ($1^{st}$ column then $2^{nd}$ column etc.)
2. Let Smooth_s be the result of applying a moving average filtering to the vector s, using a window of size between 6 and 10, or any other smoothing kernel of similar scale.
3. SMX is equal to the maximum of the absolute value of the elements of Smooth_s.

SNR can be computed by the following procedure:

Since the T2 series in each row of the S matrix decays to nearly zero at the end, due to the relatively long relaxation time, it can be reasonably assumed that the last few columns of the S matrix include mostly noise with negligible intensity means. By "last few columns of S" is meant a block of columns consisting of the columns p, p+1, ..., ns2, wherein the number of columns in said block is about ⅕ to 1/10 of the total number of columns in S (that is, 1/10≤(ns2−p)/ns2≤⅕). Next, the standard deviation of the elements in said block organized in a vector form with length n, n=ns1×(ns2−p), is calculated. For example, in order to compute the noise level in the measurement signal S, we choose to compute the standard deviation of a block consisting of ⅛ rightmost columns of S, using the standard formula for standard deviation (std) computation of a time series:

$$std = \sqrt{\frac{\sum_{j=1}^{n}(x_j - \bar{x}_n)^2}{n-1}}, \; \bar{x}_n = \frac{\sum_{j=1}^{n} x_j}{n}$$

Then SNR needed for determining the penalty weights is obtained upon dividing SMX by std:

SNR=SMX/std.

Turning to the minimization problem (1), upon organizing the ns1×ns2 samples of S into a vector s=vec(S) with length sn, wherein ns=ns1×ns2, then (1) can be reduced to the following form:

$$\min_{f,c,r} \lambda_1 \|c\|_1 + \frac{1}{2}\lambda_2 \|c\|_2^2 + \frac{1}{2}\|r\|_2^2 \quad (3)$$

$$\text{s.t.} \; Kf + r = s,$$

$$-f + Bc = 0, f \geq 0,$$

In (3), the matrix K is the Kronecker product of the previously defined matrices $K_1$ and $K_2$; hence K consists of ($ns_1 \times ns_2$) rows and ($nf_1 \times nf_2$) columns. K operates on the solution vector f, and r=vec(R) is vector representation of the residual (noise) matrix R (again concatenated column by column).

Problem (3) is solvable using available optimization routines, for example, PDCO (MATLAB optimization routine), as shown in Example 6 below. It should be noted that alternative computational approaches may be used other than explicitly constructing the matrix K. For example, some solvers such as the aforementioned PDCO allow use of an operator function that computes the matrix-vector products Kx and K'x (K' designates K transpose) given an input vector x of appropriate size. Using an operator function instead of the explicit form of the matrix K reduces significantly the running time of the solver as well as memory requirements. The operator function for K can compute Kx by rearranging the vector x as a matrix at the appropriate dimensions and then apply $K_1$ and $K_2$ from the left and right of the matrix respectively and at the end rearrange the resulting matrix as a one long vector.

A particularly preferred approach to solving the problem recognizes that the matrix K has the tensor product form $K = K_1 \otimes K_2$, where $K_1$, $K_2$ are matrices of low rank that can be exploited via SVD factorizations. Hence, this structure of K can be used to achieve high efficiency. Otherwise, if K is used directly, for example, in the manner implied by the aforementioned US 2016/0170065, it would be a large dense matrix requiring much computation and storage. PDCO is designed to accommodate structure in K as well as general bounds on f (including f>=0).

Hence, K1 and K2 can be replaced by their low rank SVD approximation. The SVD decomposition is a well known and established mathematical method which allow to take any matrix A and decompose it into 3 components, A=U*S*V' where U and V are orthogonal matrices and S is a diagonal matrix with non-zero diagonal elements decreasing in magnitude from top to bottom. In Matlab for example this is done using the command [U,S,V]=svd(A); One of the most important features of the SVD of a matrix is the ability to determine the best low rank approximation for a given matrix for any rank r which is lower than the original rank of the matrix A. We denote the best rank r approximation for a matrix A by Ar. It is best approximation in the sense that the sum of squares of the residual R=A−Ar is the lowest compare to any other rank r matrix. Ar is defined as the sum of r rank 1 matrices according to:

$$A_r = \sum_{j=1}^{r} \sigma_j u_j v_j^*$$

Where uj and vj are columns of U and V respectively and $\sigma_j$ are the diagonal elements of the matrix S.

The reason for replacing a matrix with its low rank approximation also known as SVD compressed form is that by doing that the conditioning of the matrix increases due to elimination of zero or nearly zero singular values (the diagonal elements of S) and therefore improve of the robustness and decrease the sensitivity to noise in the measurements when solving a linear system such as the NMR related one.

Another approach to improve the solution is to set to zero all values in the matrix S where T2>T1.

It should be also noted that in many cases, the simplest dictionary B=I is used (where I is the identity matrix). Alternatively, B can be a dictionary of 2D wavelet functions. It is known that any smooth signal can be sparsely represented by its significant wavelet coefficients, so if B is chosen to be a wavelet dictionary, then the vector c is a sparse vector. Yet in another embodiment of the invention, B is a dictionary of 2D Gaussian functions at a variety of locations and widths.

As pointed out above, a key feature of treating the problem resides in that the solution f is known to be sparse. This property of the solution permits other approaches to be adopted to solve the problem in fairly simple cases, other than the numerical computation based on PDCO or other optimization routines. This alternative, the full subset regression approach, consists of the following steps:

1) Resize the solution matrix F into a small size of between 20 by 20 to 30 by 30.

2) Find the optimal single-peak solution, compute Akaike information criterion (AIC) (or similar) value for the match.

3) Find the optimal two-peaks solution, compute AIC (or similar) value for the match.

4) Increase the number of peaks until the AIC value starts to decrease. Then determine the optimal number of peaks.

5) Increase the solution resolution by a factor of 4 and try to split each peak into 2 peaks within its 4 by 4 block using the AIC criteria.

6) Repeat stage 5 if higher resolution is desired.

Experimental work reported below indicates that many different materials can be characterized by the invention, for example, fatty acids and fatty acid esters. A complex material consisting of a mixture of individual substances or distinct phases can also be characterized by the invention. Specific, non-limiting examples of complex materials the characterization of which is reported below include vegetable oils and animal oils; emulsions and plant seeds. Furthermore, the experimental results reported below indicate the resolving of a highly complex material such as cattle manure, into graphic spectrums of their components such as those possessing different morphologies and molecular structures (bulk, fibril, surface layers, fibril shapes) which can be identified and categorized, as explained in more detail below.

The T1-T2 based multi-dimensional spectra—in particular maps generated by solving the minimization problem (1) as described above—offer a visually attractive format for monitoring chemical processes using different approaches. The present invention is therefore related to generation of T1-T2 multidimensional maps, their interpretation and application in various fields, but not limited to, research and industrial, medical and biological fields (it should be noted that a quantitative analysis of the results based on the 2D T1-T2 relaxation study can be carried out to determine relative proton concentrations generating the different T1-T2 peaks to generate a 3-dimensional (3D) graph that gives the data obtained by the 2D T1-T2 relaxation times, with additional information on the relative population of the protons under each peak). That is, we use NMR relaxation times for creating a graph of T1 vs. T2 to show different morphological and/or chemical domains of complex mixtures identified by different T1 vs. T2 peaks. These different morphological domains may refer to, but not limited to, crystalline, partially crystalline, amorphous, and liquid crystalline, solutions, suspensions, coatings, a porous matrix with liquid and or gas within the pores, etc. The T1-T2 maps provide deeper understanding of processes involving materials undergoing chemical or morphological changes, to enable identification, control and management of critical process variables that influence the productivity of the process etc. The invention further includes using the data achieved from the 2D T1-T2 spectrum graph for further characterizing energies of interactions using T1/T2 ratio for energy of interactions plotted on a T1/T2 vs. T2 graph and the relative volumes of each peak in the T1 vs. T2 graph, which corresponds to the relative quantity of H1 protons involved in a given interaction. Thus the invention also includes computing of 2D T1-T2 relaxation method, to give a 3D mapping (T2 vs. T1 vs. relative number, which is a peak volume of protons undergoing relaxation for a given T2 vs. T1 site).

For example, one approach consists of generating the maps at different times during the progress of a process of interest, such that changes occurring with the passage of time in the positions and intensities of the peaks observed on the periodically generated maps may be interpreted to determine a key process variable or variables, e.g., one that directly influences the yield of the process or stability. Once a key process variable or combination of variables of a process of interest has been determined, it may be utilized in different ways to monitor and optimize the process.

Accordingly, another aspect of the invention is a method for monitoring a process involving a starting material undergoing a chemical and/or a morphological change upon conversion to an end product, comprising the following steps:

Generating at least one T1-T2 multidimensional spectrum (e.g., for the starting material and/or the progressively formed reaction mass), e.g., by solving the minimization problem (1);

measuring one or more peaks in said spectrum, wherein said peak(s) is/are associated with one or more process variables;

using the variable(s) of the process identified by the T1-T2 spectrum for process monitoring (e.g., predict conversion yield or track the progress of the process); and optionally modifying said process variable (for example, through modification the composition of the feedstock material to increase yield, or modification of intermediate materials to enhance rate of conversion).

It should be noted that more than one peak may be influenced by a given process variable, and multiple peaks may be followed related to one process variable.

In one embodiment, the method for monitoring a process as provided herein comprises periodically generating T1-T2 multidimensional spectra throughout the process.

Thus, with the aid of the described invented LF-NMR T1-T2 signal relaxation analysis to form T2 vs. T1 graphics of complex materials, it is possible to obtain an overall view on a single graph of the different chemical and supramolecular morphological domains, which has novel applicability in different chemical processing to form given products such as by way of example to monitor and to use the results to determine quantitatively and qualitatively the differences in starting materials and processing conditions generated during conversion.

The approach described above is especially useful, but not limited to, for monitoring processes involving biowaste conversion (e.g., cattle and farm manure and organic waste, kitchen and domestic waste, restaurant waste). The approach is demonstrated in the study reported in Example 1 below in connection with controlling and optimizing anaerobic digestion of a biomass, such as cattle manure. Anaerobic digestion of a biomass is a natural process that provides, in addition to a set of environmental benefits, a valuable product—biogas—that can be sold for producing heat or electricity. The lignocellulosic biomass consists of various polymers (chiefly cellulose, hemicellulose and lignin) with different solid phases (e.g., crystalline and amorphous phases) and varying levels of porosity and wettability. As shown in FIG. 1, T1-T2 maps produced periodically during a three week period of cattle manure anaerobic digestion exhibit ten distinct peaks assignable to ten different domains in the lignocelluloses biomass. These domains are schematically shown in FIG. 2, which provides a model of the lignocellulose biomass (including biofilm layers that are progressively formed by the bacteria involved in the aneorbic digestion). The ten distinct peaks 1-10 of the T1-T2 spectrum of FIG. 1 correspond to ten domains marked respectively in FIG. 2. Cellulose core rosette (1) is highly crystalline and covered with sub-crystalline subsurface (2-6) integrated with hemicellulose and lignin. The outer surface of lignocellulose (7, 9, and 10) is amorphous but can be divided into inaccessible surface and accessible surface. The bacteria develop biofilm layer (8), which plays a crucial role in the anaerobic digestion efficiency. As shown in the study reported in Example 1, the peak assigned to accessible amorphous cellulose (peak number 10) is a good candidate for process control, given that this peak exhibits an inverse relationship with the rate of biogas production, indicating that the fraction of the lignocellulosic biomass that consists of accessible amorphous surface plays a major role in biogas evolution (presumably because this fraction is easily subjected to bacteria degradation while other layers are much more reluctant). Hence, with the aid of the T1-T2 spectrum, it is possible to determine that the amorphous cellulose equivalent (ACE) of the biomass constitutes a key process variable, indicating bacterial activity; and as long as there is digestible lignocellulosic matter (that is, amorphous surface cellulose) there will be bacterial hydrolysis and its rate and potential could be evaluated with ACE measurement. Hence, the initial amount of ACE in the starting material could be measured in advance to predict the biogas yield potential, such that the starting material may be pretreated to reach a threshold amount of ACE material (e.g., by supplementing the starting material with suitable additives). As explained in detail below, in the process of anaerobic digestion, amorphous cellulose is being constantly consumed (by bacterial hydrolysis) and generated (on account of conversion of other phases into amorphous cellulose). Periodic measurements of ACE on the basis of the intensity of the corresponding peak in the T1-T2 spectrum could be used to indicate whether the rate of biogas production correlates well with ACE. When the rate of biogas evolution is not as high as one would expect in view of the amount of ACE measured, then the cause for insufficient production rate should be determined and the process modified accordingly. For example, the problem may reside in insufficient accessibility of amorphous cellulose surfaces to the bacteria (e.g., because of biofilm deposition, as also suggested by the ss-C13 NMR spectrum shown in FIG. 3), in which case the engineers and production managers can improve the process by treating the biomass to remove biofilm, to expose fresh amorphous cellulose surfaces with increased accessibility to bacteria.

The experimental work reported herein shows the potential and versatility of $^1$H LF-NMR T1-T2 relaxation technology, which is relatively inexpensive lab top equipment that uses no treated samples (or with simple treatment like, but not limited to, water addition), under ambient conditions, in forming clear and reproducible T2 vs. T1 graphics of different morphological domains in lignocellulose biomass and in very complex mixtures such as cattle manure. It has also shown that it can detect changes in the morphology due to hydrolysis during conversion into fuel and can identify other films or morphological domains being generated that enhance or can block further conversion into biofuels. The low conversion rate of cattle manure into methane by anaerobic digestion was well defined by the morphological mapping of the chemical composition of lignocellulose. Using supportive data and particularly $^{13}$C ssNMR the morphological mapping could show how the supramolecular chemistry of lignocellulose's cellulose elementary fibril crystals gave a particular complex supramolecular organizational packing of the nano-aggregates. One factor we could characterize with respect to parameters that limit the fuel conversion efficiency was in anaerobic digestion of bacterial biofilm formation on cellulosic polysaccharides and the formation of epoxy oligomers. The sites of lignin cellulose interaction with the biofilm could be identified and the reduction of hydrolytic enzymatic hydrolysis rationalized by this interaction, enabling modification of the process as described above.

Hence, the method of the invention is suitable for monitoring processes involving a starting material undergoing a chemical and/or a morphological change upon conversion to an end product, and specifically, anaerobic digestion of a biomass; biodiesel production; and oxidation reactions.

Another aspect of the present invention is a method of screening chemical additives to determine their ability to inhibit a chemical reaction that a substance of interest is susceptible to undergoing (for example, degradation due to oxidation), or advance a chemical reaction that a substance of interest is being considered as a candidate for, comprising the steps of:

exposing a mixture of the substance and a tested additive to conditions of the chemical reaction under consideration;

generating a T1-T2 map for said mixture;

comparing one or more spectral features exhibited by said T1-T2 map with corresponding spectral features observed either in a first reference T1-T2 map of the intact substance, a second reference T1-T2 map of the substance when exposed in the absence of the said additive to the conditions of the chemical reaction under consideration, or with both reference maps; wherein increased similarity with the first reference map indicates that the tested additive can be used as a stabilizer and increased similarity with the second reference map indicates that the tested additive does not interfere with or promotes the reaction under consideration.

Spectral features that could serve for the comparison include shift in peak positions, formation of new peaks and changes in peak intensities. For example, with the aid of the T1-T2 spectra, it is possible to assess the stabilizing effect of the tested additive on a substance of interest, that is, the ability of the additive to minimize undesired reactions, such as, but not limited to, decomposition/degradation of the substance of interest due to oxidation reactions that may occur during storage or shipping. Hence, additives that could benefit from the invention include antioxidants. That is, a suitable antioxidant should be able to minimize changes occurring due to oxidation indicated by peak shifting, change in peak intensity and new peak generation. High similarity between the T1-T2 map of the intact, non-oxidized material and the T1-T2 map of the material exposed to oxidation conditions in the presence of the tested antioxidant indicates suitability of the additive as an effective stabilizer.

Many materials require the presence of a stabilizer when formulated, stored and shipped, for example, but not limited to, biodiesels, food ingredients, pharmaceuticals, cosmetic preparations are all prone to undergoing degradation due to, for example, oxidation. Materials possessing aggregate structures with polyunsaturated fatty acids (PUFA), found in many biological systems and commercial products, are especially susceptible to oxidation. Antioxidants may be primary or secondary. In the initiation and propagation steps, secondary antioxidants react with PUFA/lipid, peroxyl and alkoxyl radicals, preventing further decomposition into aldehydes and other volatile oxidation products. Primary antioxidants can inhibit lipid oxidation by several different mechanisms including chelation of transition metals, singlet oxygen quenching, and oxygen scavenging. Some secondary antioxidants are able to regenerate primary antioxidants in a synergistic manner, and vice versa. Some antioxidants such as melatonin can be both primary and secondary antioxidants. In food systems, metal chelators, which prevent the metal ions from decomposing lipid hydroperoxides to reactive radicals, are often very important primary antioxidants, examples of which are synthetic ethylenediaminetetraacetic (EDTA), and natural polyphosphates, phytate, caseinate, and lactoferrin. Polyphenols are often multifunction antioxidants with both free radical scavenging and metal chelating properties. Both secondary and primary antioxidants may be tested, identified and quantified for efficacy by the invented process and technology of morphological and chemical domain mapping. Another important embodiment of the present invention is its use for the identification of antioxidant combinations with enhanced efficacy beyond each of the individual components. Non-limiting examples of potentially useful antioxidants that may be characterized for efficacy by the invented methodology are melatonin, tocopherol, tyrosol, hydroxytyrosol, gallic acid, ascorbic acid, Vitamin E, beta-carotene, Coenzyme Q (10), Vitamin C, Glutathione peroxidase, Superoxide dismutase, Catalase, ethylenediaminetetraacetic (EDTA-), and natural polyphosphates, phytate, caseinate, and lactoferrin.

The method of the invention makes it possible to graph a 2D and 3D morphological spectrum of distinctive individual T1 vs. T2 relaxation time domains, on a given map, assigned to the different molecular and nano aggregate morphologies within the aggregate complex, enabling different applications/approaches to benefit from the spectrum:

1) measurement of position (T1, T2), size and intensity of the different T1 vs. T2 domains in the 2D and 3D morphology relaxation spectrum;

2) analysis of each domain for specific molecular composition and morphology by material spiking, extraction, and analysis by FTIR, HF H1 and C13 NMR XRD, and 3) use of the T1/T2 ratio as a measure of interaction energy with adjacent domains of different morphological structures within a given aggregate.

Many different material systems and conditions of material systems may be studied in this manner. For example, but not limited to, each of the approaches 1 to 3 can be implemented with the aid of measurements conducted under different conditions, such as but not limited to amphiphilic/water ratios, to see how water affects morphology and structure and which domains are reduced, stay the same, grow or are new, and differences in interaction energies (T1/T2) and the kinetics of individual domain and total aggregate changes. Analysis by FTIR, HF H1 and C13 NMR XRD of individual domains is carried out and then for other samples the specific T1 vs. T2 is already assigned to a given morphology or chemical composition. Thus once a dictionary of each T1 vs T2 domain in the graph is established it can be used with other samples or complex material and aggregates of the same category as the material used to form said dictionary of peaks assignments but of different batches without, or minimal, further use of FTIR, HF H1 and C13 NMR, XRD or other independent analytical methods. Thus, a useful feature of the present invention is that for each category of materials under consideration, a collection of characteristic T1-T2 peaks may be established and arranged in an easy-to-understand "dictionary-like" format such that any future assignment of peaks in T1-T2 maps generated for a material belonging to said category can be conveniently accomplished with reference to that dictionary.

Analysis according to the third approach—T1/T2 ratio— is a useful tool offered by the present invention. In liquid bulk, T1=T2. Reduced T1 and T2 relaxation times are observed when liquid molecules adsorb on a solid surface due to a change in the molecular mobility; (e.g., rotational correlation time). However T2 is further influenced by additional factors (e.g., translational correlation time). Thus for absorbed molecules T1>T2, because changes in the translational and rotational dynamics of the absorbed molecules influence and reduce T2 more than T1. An additional factor in porous materials with a high surface-to-volume ratio, S/V, the observed relaxation rates are proportional to S/V, so absolute T1 and T2 measurements cannot be readily used to compare interactions between materials with differing pore geometry, pore size and density of adsorption sites. However, the ratio of relaxation times T1/T2 is (to leading order) independent of these characteristics and can be used to monitor a process of interest.

More specifically, the ratio of T1/T2 can effectively be used to characterize the strength of different absorption and as a measure of adsorption energy terms. A relationship between surface relaxation and adsorption energy (E) can be derived to give T1/T2 proportional to $1/\Delta E$ and a dimensionless surface interaction parameter esurf=−T2/T1 has been defined for the purpose of interpreting surface relaxation as a surface energy.

Accordingly, another very important result of the invented T2 vs T1 graphics is the quantification of supramolecular interactions using T1/T2 ratios, which may be used to determine energy interactions and a parametric characterization of activation energy of the interaction between water (as an non-limiting example) and the absorbent (e.g., cellulose or lignin) can be used to choose optimal absorbents (such as for water uptake or surface catalytic reactions), and T1 and T2 can also be used to characterize the porosity water uptake differences between the different supramolecular morphological domains, which is very important for enzymatic accessibility and hydrolysis. A process of interest may be better advanced upon treating starting and/or intermediates materials to increase or decrease the measured T1/T2 ratio (with the aid of pH adjustment, temperature adjustment or any other reaction condition). In this way, the T1/T2 ratio measurable by the invention can be used to monitor the progress of a chemical process of interest.

The ability to show a) reproducibility and clearly the many different morphological domains in complex mixtures such as, but not limited to, cattle manure (CM) by 2D T1-T2 relaxation mapping and b) to identify water accessibility into each morphology and the strength of water interactions, and c) to follow changes in the morphologies and energy of interaction as well as d) the formation of new components, is unique compared to other spectral analysis methods and is very useful in choosing materials and procedures such as pretreatment or during the conversion process to maximize conversion efficiency. By way of a non-limiting example: the use of 2D in T1-T2 relaxation mapping of morphologies and water interactions with each morphology allows for understanding the current efficiency limit of 20% of CM conversion into methane by AD, and offers a rational approach to developing processes with enhanced efficiencies such as reduction of biofilm formation, which can be readily followed by this approach. The use of LF-NMR T1-T2 relaxation technology has very high potential as an easily used table-top biosensor instrument for bio refineries and many other industries as well as the development of processes with greater efficiency. Another very important application but not limited to is identification of antioxidants or antioxidant mixtures for the prevention or minimization of oxidation in relatively simple and complex materials found in products and systems including biological systems and product materials that contain double bonds such as mono-unsaturated and polyunsaturated alkyl chains.

As pointed out above, T1-T2 two dimensional (2D) spectra can be presented in the form of maps having T1 relaxation axis and T2 relaxation axis, thus offering a visually attractive format. But other representations are also acceptable; for the sake of simplicity, terms such as "displaying the spectrum in the form of a map" and the like used herein are meant to include equivalent representations indicating the positions of the peaks. Furthermore, the invention enables peak quantification and generation of 3D spectrum (e.g., maps or equivalent representations) indicating the intensity of the peaks. That is, an important aspect of the present invention is generating 3D spectrum graphs by assignment of signal volume in the 2D $T_1$ vs $T_2$ spectrums, which is in effect the concentration of 1H involved in the $T_1$ vs $T_2$ signal to compare the relative volumes of the different $T_1$ vs $T_2$ domains. Peak volume is an important material characterization value as it is related to the relative amounts of different morphological and chemical domains in a given material or substance. This can be used to characterize different batches of the same material categories as a quality control and/or identification of additives/modifiers to stabilize or upgrade the product. The relative changes of different morphological and chemical structure undergoing a chemical or physical change or alteration can also be identified. Quantification analysis of $T_1$ vs. $T_2$ peaks from the 2D graph was achieved by measuring the samples in $^1$H LF-NMR with fixed receiver gain (RG). RG controls the amplifying of signals acquired by the NMR therefore RG must be kept fixed in order to quantify NMR signals with the same amount of amplification, as illustrated in Example 1, Table 2.

As pointed out above, the present invention allows the resolution of chemical and morphological domains of complex materials. A complex material generally consists of a mixture of individual substances, and/or distinct phases and/or distinct morphological domains. Different morphological domains may refer to, but not limited to, crystalline, partially crystalline, amorphous, and liquid crystalline, solutions, suspensions, a porous matrix with liquid and or gas within the pores, etc. This also includes domain size and arrangement with respect to each other, and varying levels of porosity and wettability as a function of chemical structure and morphology. Complexity also includes ordered nano, meso and micron structures of amphiphiles, in aqueous solutions forming micelles, vesicles, particles, liposomes, etc. as determined by concentration and molecular packing parameters, etc. Amphiphiles in non-aqueous solutions, or as relatively pure bulk liquid of the given amphiphiles such as but not limited to liquid fatty acid, may have multiple arrangements as for example, but not limited to liquid crystalline like structures, and segmental aggregates of different parts of the molecule.

As pointed out above, the creation of a dictionary of chemical and morphological assignment per T1-T2 peak for a given material category constitutes an important contribution of the present invention. For example, the dictionary may include specific sites on a molecule such as but not limited to chemical sites on lipids or aliphatic chains such as H1 attached to the head groups on fatty acids or on the glycerol moieties of lipids, or on the double bond —C═C— or on non-saturated portions of the aliphatic chains. Different lipids and oils and other materials can be characterized with respect to variations in their chemical structures such as the different amounts of double bonds in the aliphatic chains and different head groups. The study of lipids and oils does not require the addition of water such as in the examples we give with biowaste. Experimental work reported below shows that oils such as fatty acids (short, mid and long chains, saturated and unsaturated, e.g., oleic, linolenic and erucic oils) and complex oil mixtures such as linseed oil and rapeseed oil, and food materials based on complex emulsions such as mayonnaise and butter, and natural biological materials such as lentils, hummus, chickpea seeds and castor seed, living systems such as red microalgae, can be characterized and monitored by the method of the present invention, e.g., to characterize materials for quality control, shelf life stability and transformation under chemical changes such as oxidation. FIGS. 9A to 9G depict the structures of fatty acids which were successfully resolved with the aid of the method of the invention: Octanoic acid (C8:0); Decanoic acid (C10:0); Palmitoleic acid (C16:1, cis 9); Oleic acid (C18:1, cis 9); Linoleic acid (C18:2, cis 9,12); Alpha Linolenic acid (C18:3 cis 9,12,15); and Erucic acid (22:1, cis 13). The structures depicted in FIGS. 9A-9G refer to the head-to-head dimer assembly of fatty acids known to exist in the liquid phase. The distinct domains identified in each fatty acid by the method of the invention are circled; further analysis (peak position) can be found in Example 4 below.

Biofilms generated from microbes such as bacteria can be detected on $T_2$ vs. $T_1$, 2D and 3D spectra. The observed peaks may be assigned to alkyl chains and/or proteins. In one non limiting example of such an application are biofilms generated during anaerobic digestion of bio waste into bio-fuels. This invention can also be used for detecting biofilms on other materials such as in/on food which would be an indication of bacterial or microbial contamination. This can also be used to determine specific bacteria as different bacteria will have different biofilms and thus different peaks in the T1 vs. T2 spectra. In addition to detection of biofilms of bacteria the present invention may also be used to detected whole bacterium during different stages of their life cycle. The present invention also includes infestation detection from microbes (e.g., fungi) and viruses and worms and insect larvae and their eggs, can also be detected. By the present invention the life cycle of insects (eggs, larvae, to fly) can also be monitored on substrates such as food. Thus the present invention is a powerful and unique tool for quality control and safety analysis in the, but not limited food, pharmaceutical and cosmetic industries. Examples of such applications are specifically shown in the example section for bio waste conversion to biofuel and oxidation and antioxidant prevention of oxidation bio oils used for generating biofuel.

An embodiment and application of the present invention is the detection of a wide range of bacterial populations (e.g., Salmonella, etc) in different food products, with simple real time measurements, as a quality control method.

Since the methods according to the present invention as described herein produce the three-dimensional (i.e. T1, T2, and intensity) data with unexpectedly high resolution, these data can be used to identify a fingerprint of the tested material, as generally shown herein. Such fingerprint identification of the materials may serve for the purposes of quality control of products. It has been shown that not only the material may identified, but also the deviations from the material, e.g. oxidation of the material, can be successfully demonstrated by the methods of the present invention. The quality control may be performed for a finished product, e.g. at the end of a manufacturing process. Alternatively or additionally, the quality control may be performed in process (i.e. what is known as IPQC—in-process quality control) of the manufacturing of a product. The quality control may also be performed as raw material acceptance test, e.g. when a raw material for a process arrives to the manufacturing premises. The specifics of the quality control applications will be generally governed by the relevant regulations in the target industry.

Generally, quality control methods according to the invention comprise acquiring relaxation data of product, which can be a starting material or mixture, a final material or mixture, or an intermediate mixture of a process, and converting the relaxation signals into the three-dimensional distribution of peaks having specific coordinates, intensity, and volume. These data may then be compared with the data obtained for the product or mixture of known quality, e.g. visually, or by means of a statistical test, to determine the quality of the tested product. The determination may then result in making a decision whether the tested product is of an acceptable quality and should be approved for further use, or of an unacceptable quality and should be rejected.

The data for the comparison may comprise a single characteristic, e.g. a single peak, that has a discriminative power to identify the approvable product from the rejectable product. The characteristic may include the coordinates of a peak, peak's intensity, or both. Sometimes, more than one characteristic will be used to discriminate between the approvable product and a rejectable product, e.g. a set of coordinates and intensities. The comparing of the characteristic may involve a statistical test that compares the obtained characteristic with a distribution of this characteristic in a population obtained from the products of known quality, to ensure that the discriminating characteristic is supporting the approval or rejection of the tested product.

The products tested by the quality control may be food products. The food products comprise fatty acids, oils, complex oil products, such as mayonnaise or bovine cream butter. Other food products may be also suitable for the quality control with the methods as described herein, provided a discriminative characteristic is identified for such products. The food products may also comprise seeds, such as castor seeds (Ricinuscommunis), chickpeas seeds (Cicerarietinum, alias hummus), or lentils seeds (Lens culinaris). Additionally, the products may comprise complex nutrient precursors or food additive mixtures, such as Fenugreek seeds (Trigonellafoenumgraekum), or dried powder of red microalgae Porphyridiumcruentum.

Accordingly, one specific aspect of the invention is a method of monitoring quality of a product to enter a process or to result from a process, said method comprising:

a) acquiring relaxation data of said product using LF-NMR;

b) generating at least one T1-T2 multidimensional spectrum by the methods set forth above;

c) identifying one or more characteristics of said product within said multidimensional T1-T2 distribution, d) comparing said one or more characteristics of T1-T2 distribution with respective characteristics obtained from a product of acceptable quality, and e) making a decision whether the product should be approved, rejected or modified (e.g., by addition of stabilizers).

For example, the product may be a food product, a food additive, a nutrient precursor, a fuel product, a pharmaceutically active compound or a pharmaceutical preparation, a cosmetic, etc.

EXAMPLES

Example 1

Figure 1:
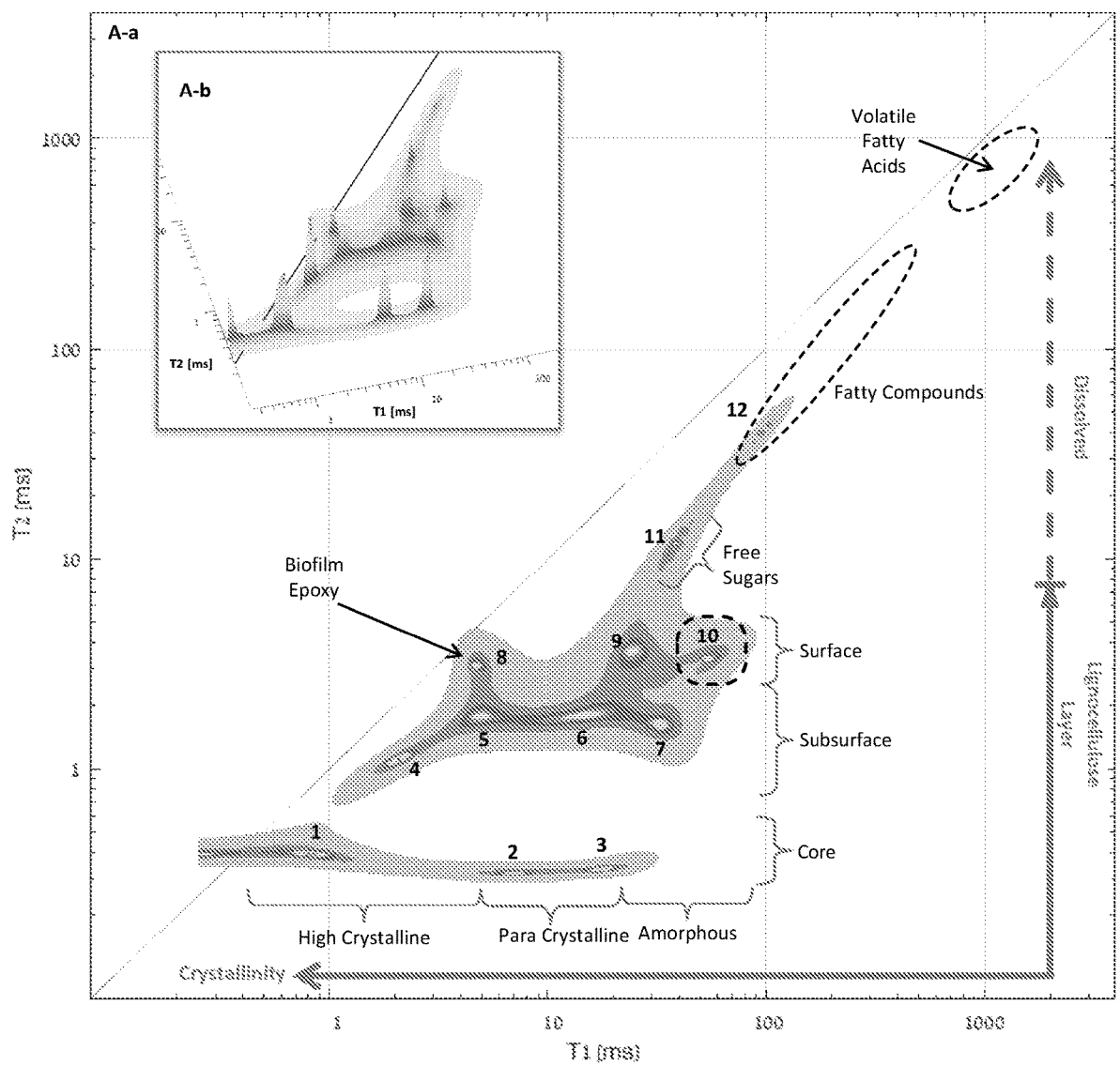
FIG. 1 shows T1-T2 multidimensional (2D and 3D) spectra in the form of maps having T1 relaxation axis and T2 relaxation axis.
Figure 2:
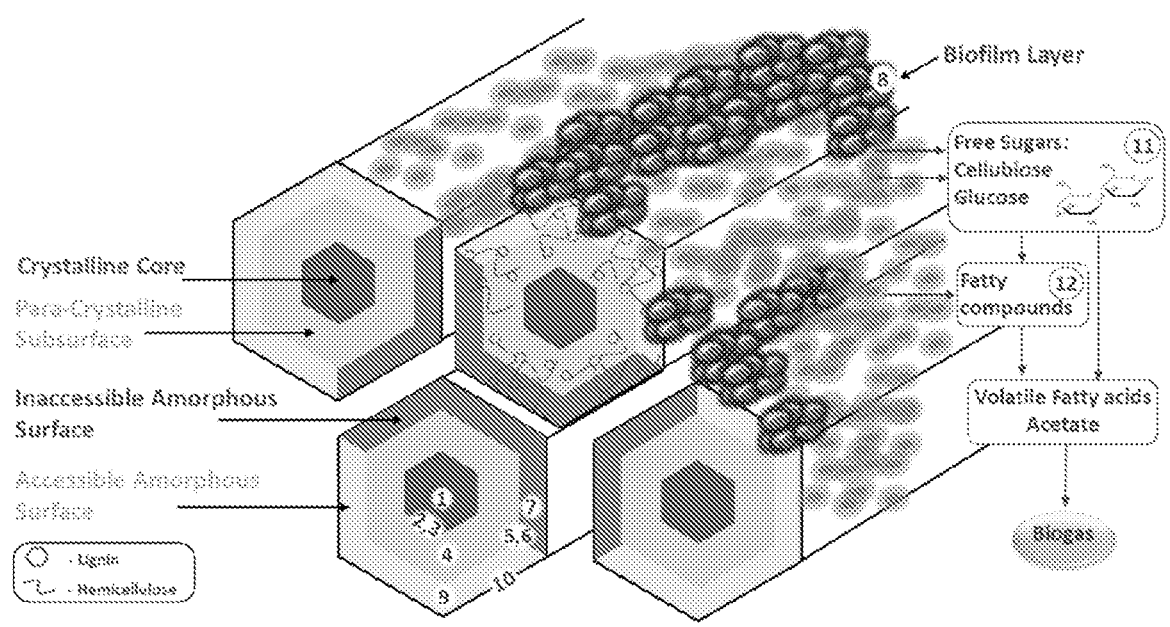
FIG. 2 shows the ten domains that correspond to the ten distinct peaks 1-10 of the T1-T2 spectrum of FIG. 1.
Figure 3:
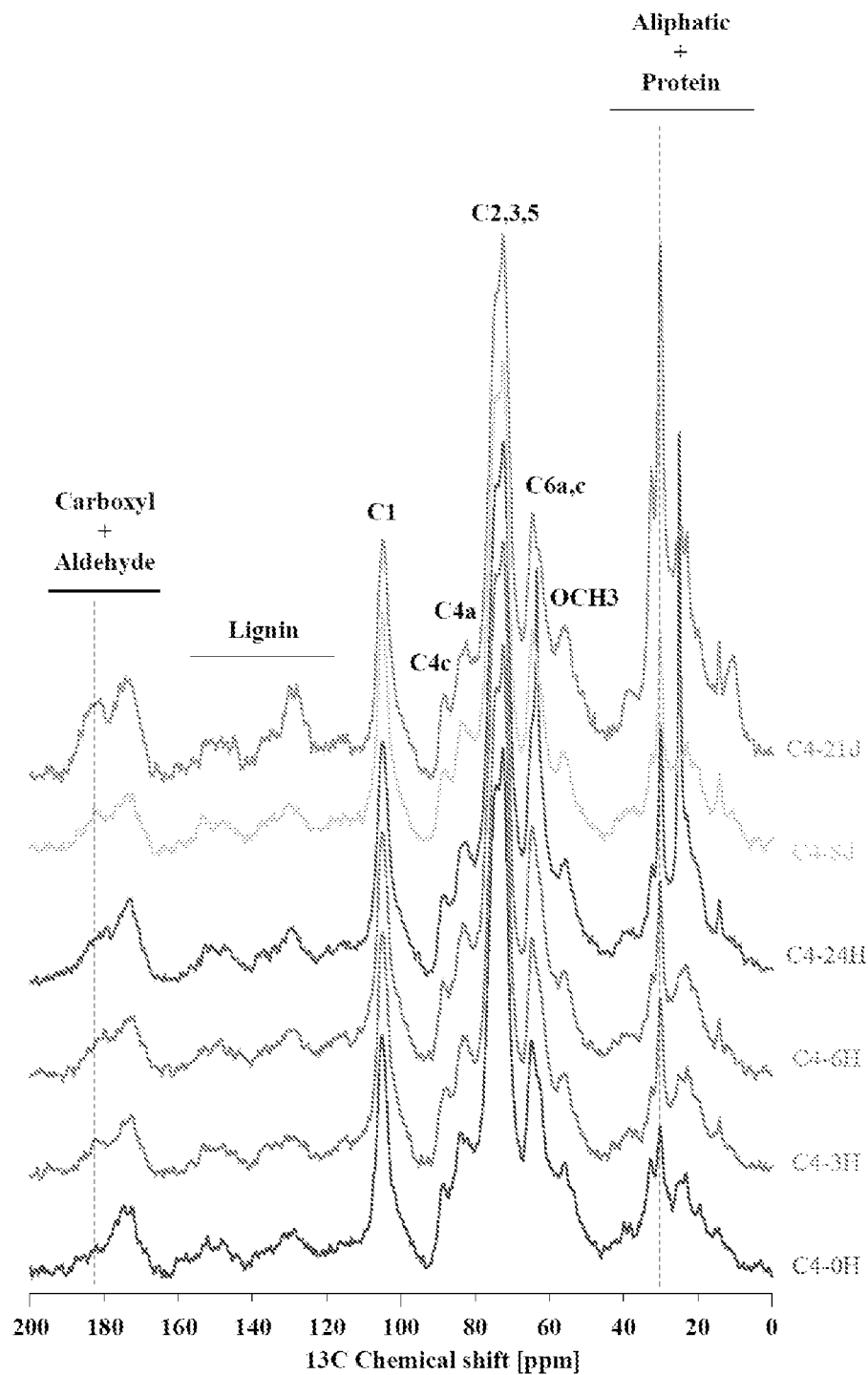
FIG. 3 is ss-C13 NMR spectrum of the Lignocellulosic component.

Anaerobic Digestion of Cattle Manure to Produce Methane

This example illustrates the application of $^1$H LF-NMR spectroscopy and signal analysis employing the mathematical method described hereinto generate a T1-T2 map and enable the monitoring of a process of anaerobic digestion of cattle manure to produce methane.

Anaerobic Digestion System

Cattle manure was collected from a district plant treating 600 tons of cattle manure per day. The cattle manure was taken from the underground preliminary tank, where the raw cattle manure is mixed with water to total solids of content ~10% by weight. Anaerobic digestion experiments were performed in a small-scale pilot plant in a laboratory at I.T.B LTD Israel. The pilot plant consists of a 30 L digester with temperature control, mixers and biogas flow meters. All digestion tests were performed at batch and mesophilic conditions for a period of 21 days. Samples were taken for chemical and physical analysis at t=0 and after 3, 6 and 24 hours and 8 and 21 days. Solids analysis of total solids and volatile solids were carried out according to standard methods (APHA 1998). Biogas flow was measured with AALBORG MASS FLOW METER GFM17. The flow meter values were collected and saved by the software RealTime Viewer 1.43 BrainChild Electronics Co., LTD.

Forage samples were collected from a feedlot of a dairy cowshed. The forage is composed of about 60% hay, 30% silage (fermented grasses and grains) and 10% grains.

Sample Preparation for $^1$H LF-NMR

All samples were completely dried at 65° C. and then ground to 0.1-1 mm particle size and kept in closed glass jars. Dried and grinded bio-waste samples were wetted to 20% moisture content (mg-water/mg-total) and placed in an NMR glass tube for conditioning at 40° C. on a heating plate for 90 minutes prior to the $^1$H LF-NMR measurement.

Signal Acquisition $^1$H LF-NMR measurements were carried out on a Maran bench-top pulsed NMR analyzer (Resonance Instruments, Witney, UK) equipped with a permanent magnet and an 18-mm probe head operating at 23.4 MHz. One-dimensional T1 relaxometry experiments were performed by repeating an inversion recovery step [180°–$t_1$] for a determined number of runs, where T1 is varied logarithmically between runs. The T1 period is dominated by spin-matrix longitudinal relaxation, including possible longitudinal cross relaxation processes. T2 relaxometry experiments were performed using a CPMG pulse sequence. This multiple sequence consists of applying a single 90° pulse followed by multiple consecutive 180° pulses. This allows measuring transverse relaxation, which results from spin-spin interactions.

2D cross-correlation experiments that demonstrate the invented signal analysis were performed by a T1-T2 sequence, where the inversion recovery step [180°–$t_1$] is inserted prior to the CPMG sequence. The $t_1$ period is dominated by longitudinal relaxation with the matrix, including possible longitudinal cross relaxation processes; while the $t_2$ period is dominated by spin-spin transverse relaxation processes.

Peak Assignment

Peak assignment was carried out using two different techniques, either (i) spiking the sample with standards of lignocelluloses components to intensify peaks or (ii) chemical removal of lignocelluloses components from the sample using hydrolysis methodologies to decrease peak intensity.

(i) Spiking of peaks was made by addition of the following standards purchased from Sigma Aldrich: cellulose fibers medium, Xylan (A hemicellulosic cell wall polysaccharide), Lignin, Pectin, pure standards of fatty acids (Acetic, Propionic, Butyric and Valeric acid). An internally laboratory-made nano-aggregated epoxy-polymer complex prepared from oxidized polyunsaturated fatty acid that was previously characterized and shown to consist of cross linked aldehyde and epoxy groups was also used as a standard. The standards were added to the dried grinded samples prior to re-watering, then the mixture was watered to desired moisture content. The addition of standard to the sample was reflected in spiking of specific peaks/areas in the $^1$H LF-NMR tests and enables characterization of the lignocellulosic appearance in the cattle manure. Once the peaks are assigned in the form of a morphological and chemical dictionary, this analysis does not have to be repeated for other samples and the dictionary is used instead.

(ii) Chemical removal of lignocellulosic components to attenuate signal peaks of $^1$H LF-NMR was achieved with the aid of the following reagents employing acceptable methods: diluted acid (HCl 2%) for hemicellulose hydrolysis;

$H_2SO_4$ 72% solution for lignin degradation (according to Kalson method—ASTM D-1106); and $HNO_3$ 70% solution for cellulose determination (according to the Kurschner methodology).

Peak Quantification

Quantification analysis was made by testing the samples in $^1$H LF-NMR with fixed receiver gain (RG). RG controls the amplifying of signals acquired by the NMR; therefore RG most kept fixed in order to quantify NMR signals with the same amount of amplification. All tests of cattle manure used in quantification of NMR signals were performed at RG=3. A calibration curve of cellulose was performed by testing samples with different amount of Cellulose standard (Sigma-Aldrich C6288) with constant RG=3.

13C-NMR CP/MAS

The $^{13}$C solid state nuclear magnetic resonance ($^{13}$C ss-NMR) experiments were carried out in a BrukerAvance 400 spectrometer, equipped with a Bruker 4-mm magic angle sample spinning (MAS) probe. The spectra were acquired with multiple-cross polarization sequence as described by O. Fričová and M. Koval'aková (2013) Solid-State $^{13}$C CP MAS NMR Spectroscopy as a Tool for Detection of (1→3, 1→6)-β-D-Glucan in Products Prepared from *Pleurotus ostreatus*. Analytical Chemistry Volume 2013 (2013), Article ID 248164, 4 pages with π/2 pulse lengths of 4 μs for 13 C (100.5 MHz) and 3.5 μs for 1H (399.9 MHz), 2 s recycle delay and 10 KHz spinning frequency.

Statistical Analysis

In order to evaluate the accuracy of our new 2D T1-T2 analysis, we have carried out three repeated measurements for each of the six instances (t=0, 3, 6 and 24 hours and 8 and 21 days) and analyzed the distribution of T1 value, T2 value and relative volume of each one of the selected 10 peaks, i.e. peaks 1, 2, 3, 4, 5, 6, 7, 9, 10, 11 (peak 8 was not detected in some test and therefore omitted). We have analyzed the data of the six instances, getting a total of 18 observations for each parameter. For each of the 3 parameters, we denote by $x_{jk}$, j=1, ..., 6 k=1, 2, 3. Let $$\bar{x}_j = \frac{\sum_{k=1}^{3} x_{jk}}{3},$$

j=1, ..., 6 be the blocks of repeated measurements average, and $$\bar{S}_j^2 = \frac{\sum_{k=1}^{3}(x_{jk}-\bar{x}_j)^2}{2},$$

j=1, ..., 6 be the sample variance for each block. Under the assumptions that $x_{jk} \sim N(\mu_j, \sigma^2)$, j=1, ..., 6 k=1, 2, 3 and that observations are uncorrelated, given standard definition and properties of the Chi Square distribution, we get $$\frac{\sum_{j=1}^{6} 2\bar{S}_j^2}{\sigma^2} \sim \chi_{12}^2.$$

We also get $$E(\hat{\sigma}^2) = E\left(\frac{\sum_{j=1}^{6} \bar{S}_j^2}{6}\right) = \sigma^2,$$

so $\hat{\sigma}^2$ is an unbiased estimator of the variance $\sigma^2$. As a result we define the following confidence intervals for the standard deviation of the estimators of each our parameters of interest:

$$P\left(\sqrt{\frac{2\hat{\sigma}^2}{\chi_{12,1-\frac{\alpha}{2}}^2}} \leq \sigma \leq \sqrt{\frac{2\hat{\sigma}^2}{\chi_{12,\frac{\alpha}{2}}^2}}\right) = 1-\alpha.$$

This confidence interval provides an estimate for the parameters' accuracy and repeatability by giving lower and upper bounds to the parameter estimator standard deviation for a given confidence level $1-\alpha$. Bounding the standard deviation of the estimators provides an evaluation of the parameters estimators' accuracy.

T1-T2 Maps

The maps (2D A-a map and 3D A-b map) are shown in FIG. 1. A total of twelve distinct peaks are identified. Since T2≤T1, none of the peaks is found above the T2=T1 diagonal. It is noted that two peaks (numbered 11 and 12 in the 2D map) are oriented along the diagonal line; these peaks are discussed later on.

The remaining ten peaks (numbered 1 to and 10 in the 2D map) are of significance because they are associated with the compositional and morphological changes occurring during the anaerobic digestion of the cattle manure. The group of peaks 1-10 can be subdivided into different domains in the map, aligned either horizontally (with constant T2 and varying T1) or vertically (with constant T1 and varying T2).

Starting with the first subdivision, three different horizontal domains are observed in the map. The first domain consists of peaks 1, 2 and 3; the second domain consists of peaks 4, 5, 6 and 7, and the third domain consists of peaks 8, 9 and 10. Peaks belonging to the same horizontal domain are assigned to aggregate structures possessing comparable porosity (hence approximately the same T2) but subjected to different environmental interactions (hence displaying different T1 values). The 1, 2 and 3 peaks correspond to similar small pore size; an intermediate pore size is assigned to peaks 4, 5, 6 and 7 whereas larger pore size is associated with peaks 8, 9 and 10.

Alternatively, analyzing the distribution of the peaks along roughly constant T1 and varying T2, then again three different domains are noted in the map. The first zone consists of peaks 1 and 4; it has the lowest T1, indicating a low relaxation time due to strong water-lignocellulose nano-aggregate interactions. The second zone consists of peaks 2, 3, 5, 6, 8 and 9. These peaks are associated with intermediate water $^1H$ aggregate interaction forces. The third zone consists of peaks 7 and 10, associated with highest level of water $^1H$ and seems to possess swollen morphologies indicating amorphous polymers.

As mentioned above, peak assignment within the T1-T2 map was achieved by means of two techniques, either by spiking the samples with known standards of the lignocelluloses components found in cattle manure, e.g., cellulose, hemicelluloses, pectin and lignin, or by chemically hydrolyzing hemicelluloses lignin and pectin using conventional reagents.

In general, as indicated by the arrows marked parallel to the axes in the map of FIG. 1, T1 increases with decreasing crystallinity of the lignocellulosic component, whereas T2 increases on moving from core domains towards subsurface and surface domains of the lignocelluloses component.

Peaks 1 and 10 are readily assignable on account of general considerations. Peak 1 has the smallest pore size and strongest interaction of water $^1H$ with the surface of the nano-aggregate material. These nano-aggregated complexes are assigned as highly crystalline cellulose interior domain. Peak 10, on the other hand, is assigned to an amorphous cellulose surface domain, as suggested for elementary cellulose fibril model. Peaks 2 and 3 have a higher T1 compared to peak 1; the increased T1 indicates a reduction of the interaction strength with water protons. These peaks are assigned to the surface of the interior crystalline cellulose domain, which consists of cellulose partially-coated/associated with hemicelluloses and pectin chains. Peak 4 is assigned as subsurface second layer suggested in the elementary cellulose model. It consists of para-crystalline cellulose tightly attached and coated with low hydrated hemicelluloses. Peak 5 fits well to a standard of oxidized polyunsaturated fatty acid domain that was especially tested in the present 2D mapping system. This standard is rich with aldehyde end groups and will be discussed in depth later on. Peak 6 is assigned to medium-hydrate para-crystalline nano-aggregated cellulose complex coated with hemicelluloses, pectin and lignin. A relatively higher degree of hydration typical for this peak is explained by the hemicellulose "loop chains" that may absorb more water in comparison to peak 4. Peak 7 is assigned to hydrated partially amorphous cellulose. Based on the polyunsaturated fatty oxidized standard test, peak 8 is assigned as surface epoxy hydrophobic nano-aggregated domain, which will be discussed in more depth later on. Peak 9 is assigned a semi-hydrated surface amorphous nano-aggregated fraction of depolymerized oligosaccharides. Peak 10 is assigned as hydrated surface of highly amorphous domain of cellulose. As summarized in Table 2, peak 10 is suggested as a cellulosic indicator of the CM components with the potential for hydrolysis and release of free sugars (glucose, xylose, etc.) shown in peak 11. Peak 12 is attributed to fatty compounds, as assigned by a standard spiking.

The data is tabulated in Table 1, which can be used to form a dictionary of chemical and morphological assignment per peak for a given material category.

TABLE 1

| Peak | "Horizontal" Domain | Lignocellulosic Component |
|---|---|---|
| 1 | C1 | Highly crystalline interior nano-aggregated cellulose |
| 2-3 | | Semi-hydrated crystalline nano-aggregated cellulose coated with hemicellulose and pectin |
| 4 | C2 | Low-hydrated sub-surface crystalline nano-aggregated cellulose closely coated with hemicellulose, pectin, lignin and may be coated with bacterial cellulosic biofilm |
| 5 | | Semi-hydrated sub-surface nano-aggregated oxidized complex containing aldehyde products of EPS biofilm |
| 6 | | Semi-hydrated sub-surface nano-aggregated of cellulose loosely coated with hemicellulos, pectin and entrapped lignin |
| 7 | | Hydrated sub-surface amorphous nano-aggregated cellulose plus loose hemicellulose |
| 8 | C3 | Low-hydrated surface hydrophobic nano-aggregated bacterial epoxy EPS biofilm complex |
| 9 | | Semi-hydrated surface amorphous aggregated oligosaccharides plus hemicellulose and trapped lignin |
| 10 | | Hydrated surface highly amorphous domain of cellulose (indicator of free sugars release) |
| 11 | — | Free sugars (mono and disaccharides) |
| 12 | — | Fatty compounds |

Figure 4A:
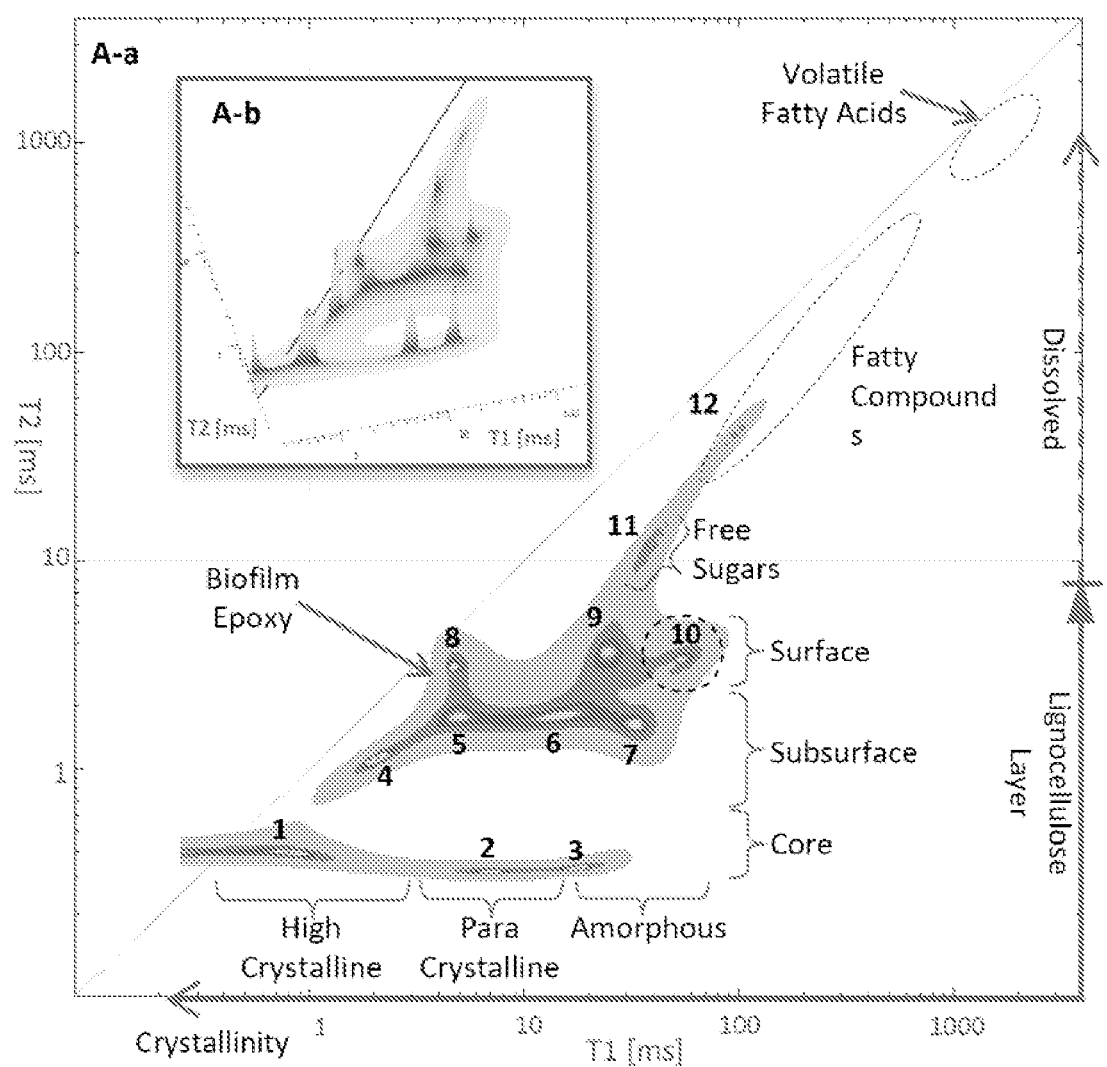
FIGS. 4A and 4B compare between the T1-T2 relaxation maps of cattle manure (4A) and forage sample (4B) prior to anaerobic digestion.
Figure 4B:
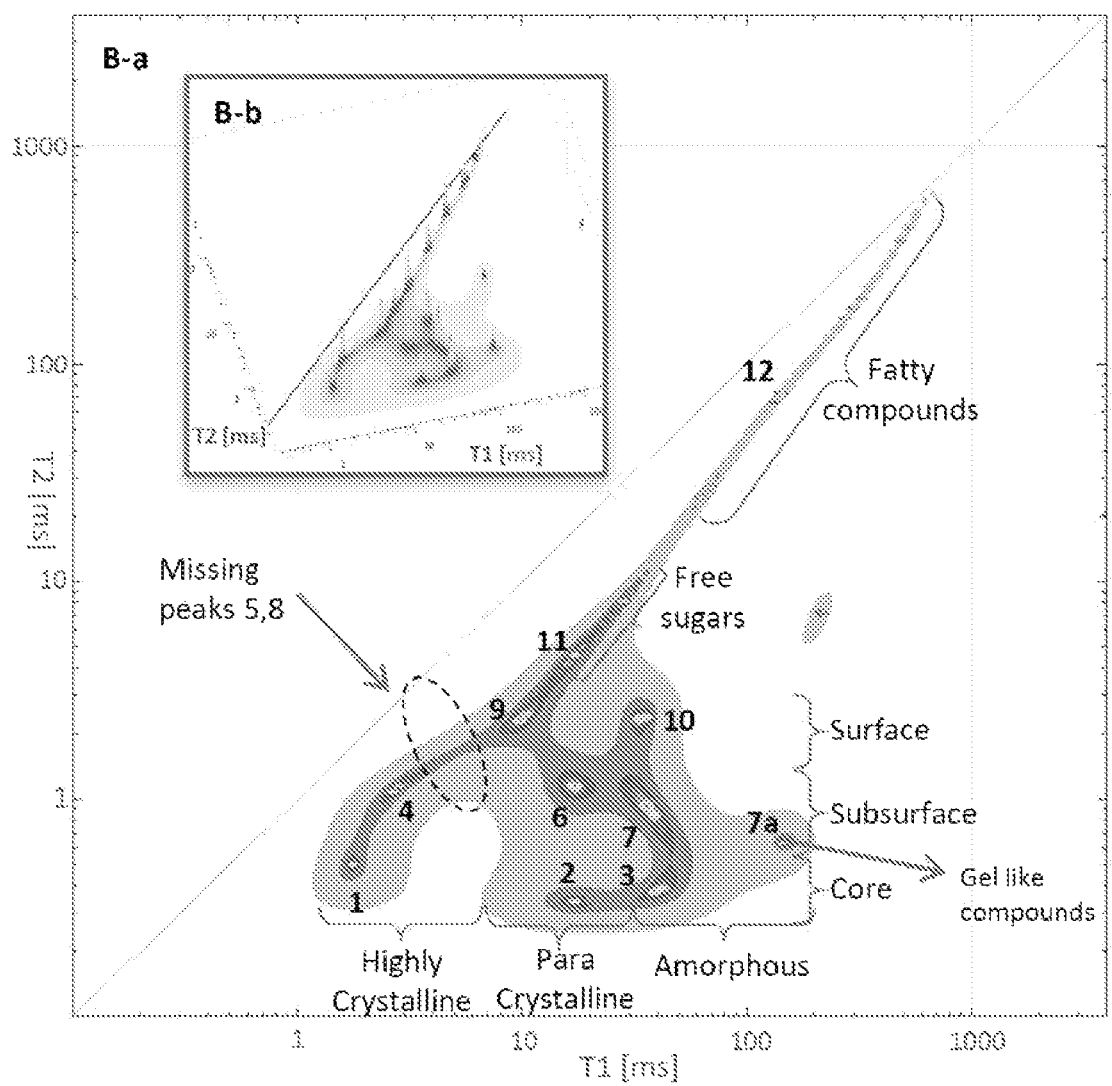

FIG. 4 compares between the T1-T2 relaxation maps of cattle manure (FIG. 4A, identical to FIG. 1) and forage sample forage sample (FIG. 4B) prior to anaerobic digestion. The latter serves as a control for the morphological spectrum changes resulting from the anaerobic digestion. It can be readily seen that the forage sample is much richer in free sugars, TAGS, conventional vegetable FAs and short FAs, which are confirmed by T1-T2 analysis of standards in comparison to CM AD. At the lower part of the diagonal a similar basic pattern similar to CM AD samples is observed. A low pore size (T2) of interior layer crystalline is seen in the contour map. A second intermediate porosity layer representing the subsurface of the elementary cellulose fibrils followed by a more increased pore size layer of the fibril surface is observed. A semi-quantitative detection shown in FIG. 4B-b clearly shows a high proton population level in the more hydrated peaks of the interior and subsurface layers in comparison to FIG. 4A-b. Based on the spiking analysis described above for CM, these peaks are assigned to high pectin associated with cellulose. Since the forage sample is rich in young vegetable grasses dominated by primary cell wall, high pectin is highly hydrated and also contains relatively high amorphous cellulose domains and may further support this assignment.

Interestingly, in the forage T1-T2 relaxation map (FIG. 4B) peaks 5 and 8 are missing, though they are clearly seen in CM map (FIGS. 1, 4A). This suggests that these peaks are related to materials formed by the AD process formed by microbial activity.

The data shown in FIGS. 1 and 4 is at the initial stage of the AD of cattle manure biomass. The pre AD stage is represented by forage sample (FIGS. 4 A and B). The 2D T1-T2 relaxation maps at each stage clearly demonstrate the stability and the repeatability of the present new morphological mapping technology. The change of signals in the spectral maps is well reflecting the surface changes including cellulose fibers degradation and microbial activity. The forage control sample clearly shows on one hand non-degraded cellulose fibers and on the other hand a very initial stage of microbial colonization. In CM T-0 sample that already went under AD process in the cattle rumen, a significant degradation is observed in cellulose fiber and a significant microbial colonization layer is seen. This pattern of both surface cellulose degradation and increase of an extracellular polysaccharide (EPS) thick biofilm layer is seen as expected. In a later stage of the present study the qualitative T1-T2 relaxation maps and peak assignment described above will be quantified and discussed.

The morphological changes that occur during decomposition of lignocellulose and releasing of biogas are directly influenced by the nano-aggregated complexes surface structure and their free surface energy and energy barriers to AD. The susceptibility to further conversion of the different nano scales of aggregate structures is rationalized by consideration of aggregate porosity of the different aggregated complexes by T2 values and interaction energy for rationalizing subsequent modifications by T1 values, which characterizes the proton interaction with hydroxyl groups of these complexes.

Another important aspect is consideration of aggregate surface hydrophobicity due to phenyl and methoxy moieties of lignin is seen through changes in the proton's motion detected by the 1D relaxation technology and further support and complement the results obtained by 2D T1-T2 relaxation spectrum generated by the presented graphic mapping with other well established spectral technologies for different specific measurements.

Monitoring and Modifying Cattle Manure Anaerobic Digestion with the Aid of a Selected Peak from the T1-T2 Map To quantify proton concentrations within each of the peak domains measured during the anaerobic digestion process, in order to enable identification of changes occurring in the corresponding morphological sites throughout the process (from t=0 to t=21 days), we performed all the tests of cattle manure samples used in quantification of NMR signals at fixed and constant receiver gain, RG=3 (in order to quantify NMR signals with the same amount of amplification).

The results are tabulated in Table 2 (expressed as relative volume of the peaks in percentages).

TABLE 2

Peaks relative volume of 3D T1-T2 relaxation map of cattle manure during anaerobic digestion.

| Time | Peak | | | | | | | | | |
|---|---|---|---|---|---|---|---|---|---|---|
| | 1 | 2 + 3 | 4 | 5 | 6 | 7 | 8 | 9 | 10 | 11 |
| 0 hr | 20.58 | 14.86 | 21.54 | 6.16 | 13.13 | 14.12 | 2.07 | 2.71 | 4.38 | 0.62 |
| 3 hr | 19.33 | 20.02 | 18.36 | 11.72 | 13.38 | 9.68 | ND | 5.87 | 0.73 | 0.92 |
| 6 hr | 21.08 | 20.62 | 16.96 | 9.46 | 12.52 | 10.96 | 3.23 | 5.10 | 1.34 | 0.89 |
| 24 hr | 21.58 | 21.04 | 16.66 | 8.65 | 11.57 | 10.82 | ND | 6.47 | 2.16 | 1.06 |
| 8 days | 22.00 | 20.44 | 15.79 | 8.55 | 10.64 | 14.63 | ND | 5.13 | 1.82 | 1.00 |
| 21 days | 25.94 | 18.47 | 21.76 | 9.74 | 9.13 | 7.05 | 5.73 | 6.63 | 1.32 | 1.26 |

The results indicate that proton populations of peaks 1 and 4 assigned as most crystalline cellulose nano-aggregated complexes are stable during most of the digestion process while peak 1 increased during the last period near to 21 days. The proton populations of peaks 7 and 10 assigned to the most amorphous morphological regions significantly decreased during the digestion process. Proton population of peaks 5 and 8, assigned as oxidized aggregated structures of bacterial EPS biofilm, show a general increase from the initial stage to the end of anaerobic digestion process at 21 day. Proton population of peak 11, assigned to free sugars that are continuously released from the amorphous fractions of the nano-aggregated cellulosic complexes and then degraded to volatile fatty acids to yield the final biogas product, have a relatively stable steady state concentration during the anaerobic process.

Peak 10 emerges from the study reported in Table 2 as a good candidate for monitoring the process, since the domain associated with peak 10 has the longest T1 and T2 relaxation times of all other lignocellulosic domains, indicating that this domain is composed of the most loosely packed and less ordered aggregate. The interaction of water molecules with the morphological site corresponding to peak 10 is therefore relatively weak, allowing higher water mobility and exchange energy with cellulose fibers surface. Furthermore on account of its amorphous character, the domain under consideration is highly accessible to water solubilized hydrolytic enzymes. Hence the domain represented by peak 10 is more readily degradable, that is, to free sugars that are further hydrolyzed to short chain volatile fatty acids such as acetate, propionate, butyrate that are used by methanogenic bacteria to generate methane.

Figure 5A:
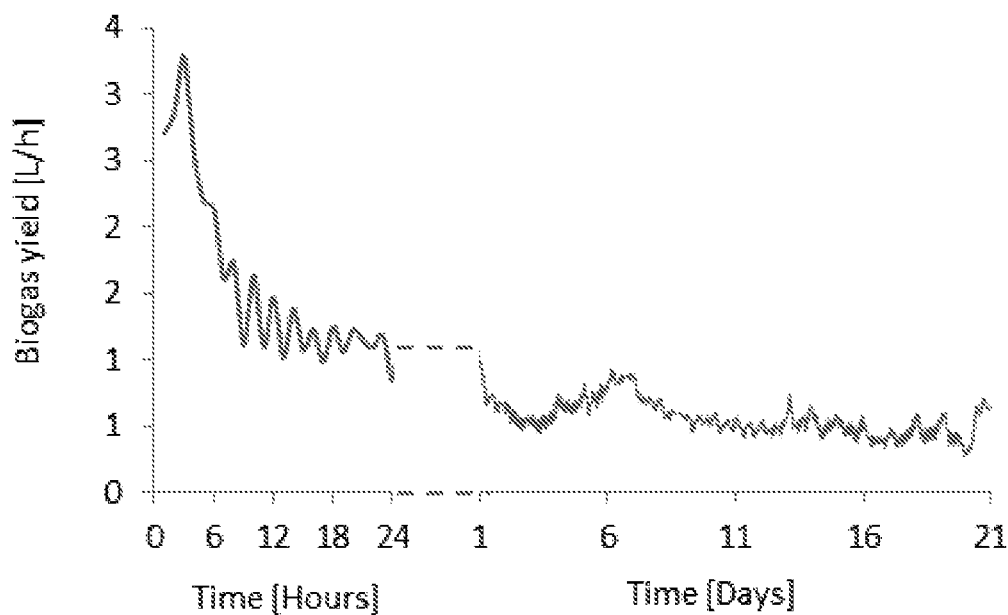
FIGS. 5A and 5B show biogas flow measurements (daily biogas flow rate in FIG. 5A and cumulative biogas yield during 21 days of anaerobic digestion in FIG. 5B), demonstrating an inverse correlation between the biogas flow and the intensity of peak 10.
Figure 5B:
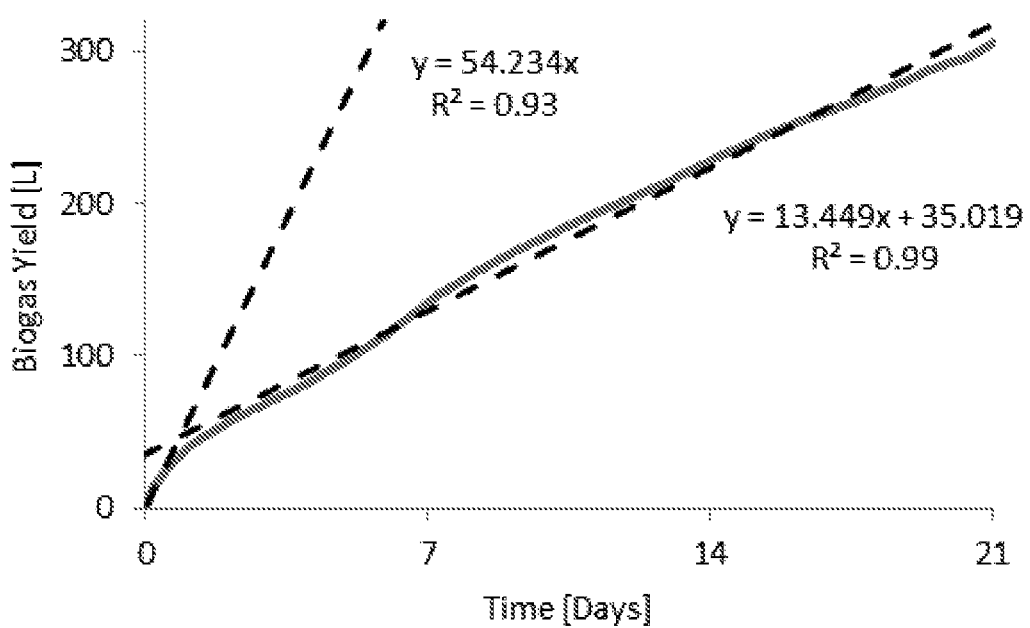

For this reason, an inverse correlation is expected between the intensity of peak 10 and the biogas flow. Biogas flow measurements are shown in FIGS. 5A and 5B (daily biogas flow rate and cumulative biogas yield during 21 days of anaerobic digestion, respectively). Indeed, in the first 24 hours, when biogas flow significantly increases to a maximum level, peak 10 decreases to a low level. Along the entire period of 21 days of the anaerobic digestion process this inverse correlation is clearly demonstrated. This finding shows that peak 10 can serve as an indicator for digestibility of cellulosic components in complex chemical and morphological mixtures.

Hence, quantification of peak 10 can be used for describing cattle manure degradability by anaerobic digestion. The quantification of glucose is also important because it is the final product of enzymatic hydrolysis of cellulose and subsequently fermented to fatty acids and methane. Hence the ability to quantitatively measuring glucose may serve as a powerful tool in cellulose hydrolysis characterization. There is strong match between peak 10 and amorphous cellulose and thus it is reasonable to consider the signals of amorphous cellulose standard as equivalence to peak 10.

Calibration curve of amorphous cellulose standard (Sigma-Aldrich C6288) in the 2D T1-T2 system was established. The signal volume of amorphous cellulose shows a highly linear fit, indicating that every 5.5 signal units of peak 10 in the 2D relaxation map are equivalent to 1 mg of amorphous cellulose. Therefore, the amorphous cellulose equivalent (ACE) of cellulosic biomass can be calculated on the basis of the intensity of peak 10, to determine concentration of ACE along the process. The results are shown in Table 3 (including the concentration of ACE in the forage).

TABLE 3

Amorphous Cellulose Equivalent (ACE) of cattle manure during anaerobic digestion and of forage.

| Time | Peak 10 Signal Intensity (AU) | ACE in a Sample mg | Total ACE % Dry | Total ACE in Digester gram |
|---|---|---|---|---|
| Forage | 2655 | 483 | 16.1 | — |
| 0 hr | 748 | 136 | 4.53 | 117 |
| 3 hr | 133 | 24.2 | 0.81 | 20.8 |
| 6 hr | 250 | 45.4 | 1.51 | 39.0 |
| 24 hr | 410 | 74.5 | 2.48 | 62.6 |
| 8 days | 332 | 60.4 | 2.01 | 47.6 |
| 21 days | 264 | 48.0 | 1.60 | 32.7 |

The ACE of the cattle manure before digestion was 117 grams; it immediately decreases to its minimum value of 20.8 grams due to a peak in bacterial activity and biogas production then slightly increases and fluctuates for the rest of the digestion period due to consumption-production fluctuated rates.

It is seen that after the sharp decrease in the first 3 hours, ACE does not decrease significantly because it is produced constantly from the transition of crystalline and sub crystalline cellulose to partially amorphous. That is, ACE of cattle manure is reduced during the process of anaerobic digestion but keeps on low value due to constant degradation of inner layers of lignocelluloses, creating new amorphous regions.

ACE is therefore an effective indicator of bacterial activity, and as long as there is digestible lignocellulosic matter there will be bacterial hydrolysis and its rate and potential could be evaluated with ACE measurement. Furthermore, the initial amount of ACE indicates the biogas yield potential. This is because in a batch anaerobic digestion process, the first phase of the digestion, i.e. first 24 hours, is the major biogas yielding phase due to degradation of the highly accessible amorphous cellulose on the outer fibril surface. In the study reported above, the initial amount of ACE was 117 grams and it produced 306 liters of biogas during 21 days of AD. Hence, the biogas yield potential calculation based on measurement of ACE is ~2.6 L-biogas per g-ACE.

It is seen that the quantification of peak 10 can serve for measuring an important process variable—ACE—which in turn can be used to predict the productivity of methane generation at an early stage of the process. Furthermore, significant reduction or disappearance of peak 10 indicates that the amorphous site has been exhausted.

Furthermore, quantification of peak 10 will also allow engineers and production managers to improve the process in different ways.

A first approach consists of pre-treating the cattle manure starting material to increase the initial amount of ACE to arrive at a predetermined threshold, guaranteeing larger conversion of the methane product to meet demand. For example, a sample of cattle manure was pretreated by soaking it in water and heating to 50° C. for 1 hour and then draining the water. The ACE of the resulting cellulosic biomass was 135 grams before digestion, and it produced 400 liters of biogas during 21 days of anaerobic digestion. The same procedure, but with an extended heating time (4 hours instead of 1 hour) afforded cellulosic biomass with ACE content of 155 grams before digestion, which produced 550 liters of biogas during 21 days of anaerobic digestion. A second approach to modify the cattle manure starting material consists of enriching it with kitchen waste. When kitchen waste was added to cattle manure (to produce a sample equal in weight to the sample studied in Table 3), the intensity of peak 10 increased, indicating an amorphous content before digestion of 160 grams. This kitchen waste-added cattle manure converted into 450 liters of biogas during 21 days of anaerobic digestion A second approach to improve the process involves a removal of the lipid-based coatings that are progressively deposited onto the surfaces of the amorphous domains, resulting in loss of accessibility of these surfaces. For example, if the measurement of peak 10 at some time of the process indicates that amorphous regions exist but on the other hand the output of the process is not satisfactory, then the coatings may be eliminated by treating with lipid digesting bacterium to expose the surface of the amorphous domain and enable the production of methane to continue. In this regard, the intensity of peaks 11 and 12 associated with the lipid generated by the bacterium may support the conclusion that the problem resides in formation of thick lipid coatings blocking the access to the amorphous regions.

Monitoring and Modifying Cattle Manure Anaerobic Digestion with the Aid of T1/T2 Ratio T1/T2 ratios were calculated for each of the morphological sites identified in the 2D T1-T2 map over the 21 days test period. The results are tabulated in Table 4.

The following trends are noted:

Peaks 1, 2 and 3 correspond to highly crystalline and semi-hydrated crystalline domains, respectively. That is, the level of crystallinity is decreased on moving from 1→2→3. It is seen that the T1/T2 ratio increases from 2 to 20 to 55 for domains 1, 2 and 3 respectively (at t=0). The same trend is seen at all stages of the AD for T2–T1 domains 1, 2 and 3. This increase is attributed to increasing T1 values, brought about by lower interaction strength of the absorbed H water protons and the environment, which we hypothesize is due to changes in the environment of the crystalline cellulose nano/micro morphologies, which lowers interactive strength and increases T1.

As shown in the 2-D T1-T2 map (FIG. 1), Peaks 4, 5, 6 and 7 located in the second T2 layer (meaning the their porosity is larger than the first layer—peaks 1, 2, 3) are less crystalline and have more amorphous nature wherein the T2 stays approximately constant. The same trend is seen with increasing T1 values with the T1/T2 ratio going from 4 to 9 to 23 respectively (at t=0). Peaks 3, 6 and 9, which are associated with the semi-hydrated amorphous sub-surface, go from more crystalline (3) to less crystalline to highly amorphous morphologies wherein the T1 is relatively constant. The T1/T2 ratio decreases from 55, 9 and 7.5 at time zero, and at time 21 days goes from 38.7, 10 to 4. The trend in T1/T2 is similar and indicates that T1/T2 is changing because of the increasing strength of interaction with the given morphology, which appears to be the strongest with the more crystalline (peak 3) and decreasing with the increase in the more amorphous morphologies and different chemical compositions such as hemicellulose and lignin. This reduction in the strength of the interaction may correspond to the increase in T2 relaxation times in the amorphous regions.

Peaks 7, 10 and 11 correspond to amorphous sub-surface, highly amorphous surface and free sugars respectively. T1/T2 ratios decrease on moving from 7→10→11 and may be due to decrease in the interactive strength of adsorbed H water interactions with the surrounding environment due to decreases in cellulosic chains and thus hydrogen bonding interactions.

If T1 and T2 both increase by the same factor, the ratio T1/T2 does not change. For example domains 7 (amorphous sub-surface) and 3 (Crystalline interior) in Table 4 have similar T1/T2 ratio from the $3^{rd}$ hour until the $8^{th}$ day, indicating similar strengths of water adsorption, though differences in morphology wherein other components in the surrounding environments may affect the results by competitive interactions with the protons interactions.

Another very important result of the T2 vs T1 graphics is that the T1/T2 ratios, which may be used to determine energy interactions and a parametric characterization of

TABLE 4

T1/T2 Ratio [ms/ms] of different morphological sites in 2D T1-T2 relaxation time of cattle manure.

| Time | Peak | | | | | | | | | | |
|---|---|---|---|---|---|---|---|---|---|---|---|
| | 1 | 2 | 3 | 4 | 5 | 6 | 7 | 8 | 9 | 10 | 11 |
| 0 hr | 2.21 | 20.81 | 54.60 | 2.00 | 3.89 | 9.15 | 23.16 | 1.60 | 7.54 | 19.92 | 3.61 |
| 3 hr | 2.40 | 17.33 | 39.94 | 2.28 | 5.64 | 14.99 | 39.94 | ND | 4.97 | 19.64 | 2.78 |
| 6 hr | 2.39 | 20.97 | 41.57 | 2.24 | 4.99 | 11.48 | 37.26 | 2.97 | 5.17 | 15.99 | 2.82 |
| 24 hr | 2.20 | 17.35 | 37.30 | 2.25 | 4.59 | 12.66 | 37.06 | ND | 4.71 | 13.49 | 2.81 |
| 8 days | 2.31 | 15.27 | 36.87 | 2.24 | 5.32 | 10.58 | 34.20 | ND | 5.12 | 15.53 | 2.75 |
| 21 days | 2.51 | 23.29 | 38.75 | 2.38 | 4.73 | 9.98 | 25.04 | 3.44 | 4.00 | 11.10 | 2.54 | activation energy of the interaction between water and the absorbent (e.g. cellulose or lignin), may also be used to characterize the porosity water uptake differences between the different supramolecular morphological domains, which is very important for enzymatic accessibility and hydrolysis. We showed that by pretreatment with water at 50 C for 20 hours the T1/T2 ratio increased and the yield of methane increased by 10%.

The values of T1/T2 in Table 4 can be correlated with the strength of the interactions between proton $H_2O$ and the surface, which can be rationalized in our study by the degree of crystallization and the number of —OH on the cellulose available for interaction with the absorbed water. Thus the higher the T1/T2 value the stronger the interaction for a given morphological domain due to the greater reduction of T2 than T1 when going from bulk water to adsorption on external and porous surfaces.

Statistical Analysis

Using the mathematical formulas and programs in the statistical analysis section the accuracy and reproducibility of the 2D $T_1$-$T_2$ analysis was evaluated. For ten different samples of CM and forage biomass three repeated measurements per sample were carried out, and the distribution of $T_1$ value, $T_2$ value and relative volume of each of the selected 10 peaks in the map (Table 1) were analyzed. An unbiased estimator of the variance $\sigma^2$ was obtained and a confidence interval for the standard deviation of the estimators of each our parameters was accepted. This confidence interval provides an estimate for the parameters' accuracy and repeatability by giving lower and upper bounds to the parameter estimator standard deviation for a given confidence level 1-$\alpha$. Table 5 shows the confidence interval lower and upper bounds of the standard deviation of the estimators of each of the 3 parameters of interest for each of the 10 peaks at 95% confidence.

TABLE 5

Variability of the estimators

| Peak | T1 | T2 | Relative Volume |
|---|---|---|---|
| 1 | [0.0167, 0.0439] | [0.0028, 0.0063] | [0.2745, 0.6318] |
| 2 | [0.4297, 0.9891] | [0.0042, 0.0098] | [0.7535, 1.7346] |
| 3 | [0.5841, 1.3447] | [0.0053, 0.0122] | [0.5772, 1.3286] |
| 4 | [0.0258, 0.0595] | [0.0091, 0.0210] | [0.3290, 0.7573] |
| 5 | [0.2316, 0.5331] | [0.0407, 0.0938] | [0.5095, 1.1730] |
| 6 | [0.7027, 1.6177] | [0.0173, 0.0398] | [0.4657, 1.0721] |
| 7 | [1.1261, 2.5932] | [0.0105, 0.0242] | [0.7823, 1.8008] |
| 8 | [0.4857, 1.1181] | [0.0844, 0.1944] | [0.5043, 1.1610] |
| 9 | [1.5586, 3.5879] | [0.0512, 0.1179] | [0.3085, 0.7101] |
| 10 | [0.8313, 1.9136] | [0.1696, 0.3903] | [0.0474, 0.1092] |

Lower and upper bounds of the standard deviation of $T_1$, $T_2$ and relative volume of each of the selected peaks with 95% level of confidence.

Example 2

Oxidation of Oils and Screening for Effective Antioxidants

To demonstrate the efficacy of a 3-D (T1, T2, intensity) map generated by the method of the invention in investigating and improving oxidation processes, linseed oil or pomegranate oil were separately oxidized at 80° C. with bubbling of air through the sample over 24 hours. The 3-D maps were created by obtaining the NMR relaxation times measurements and using the computational procedure described herein. The maps were produced for non-oxidized and oxidized samples of linseed oil (FIGS. 6A and 6B, respectively) and likewise, for non-oxidized and oxidized samples of pomegranate oil (FIGS. 7A and 7B, respectively).

Linseed oil is rich in omega-3 PUFA—the component which is susceptible to oxidation. On comparing the 3-D maps of FIGS. 6A and 6B, the oxidation of linseed oil is readily seen by the shift of the positions of peaks and generation of additional peaks in the map corresponding to the oxidized oil (6B).

Figure 7A:
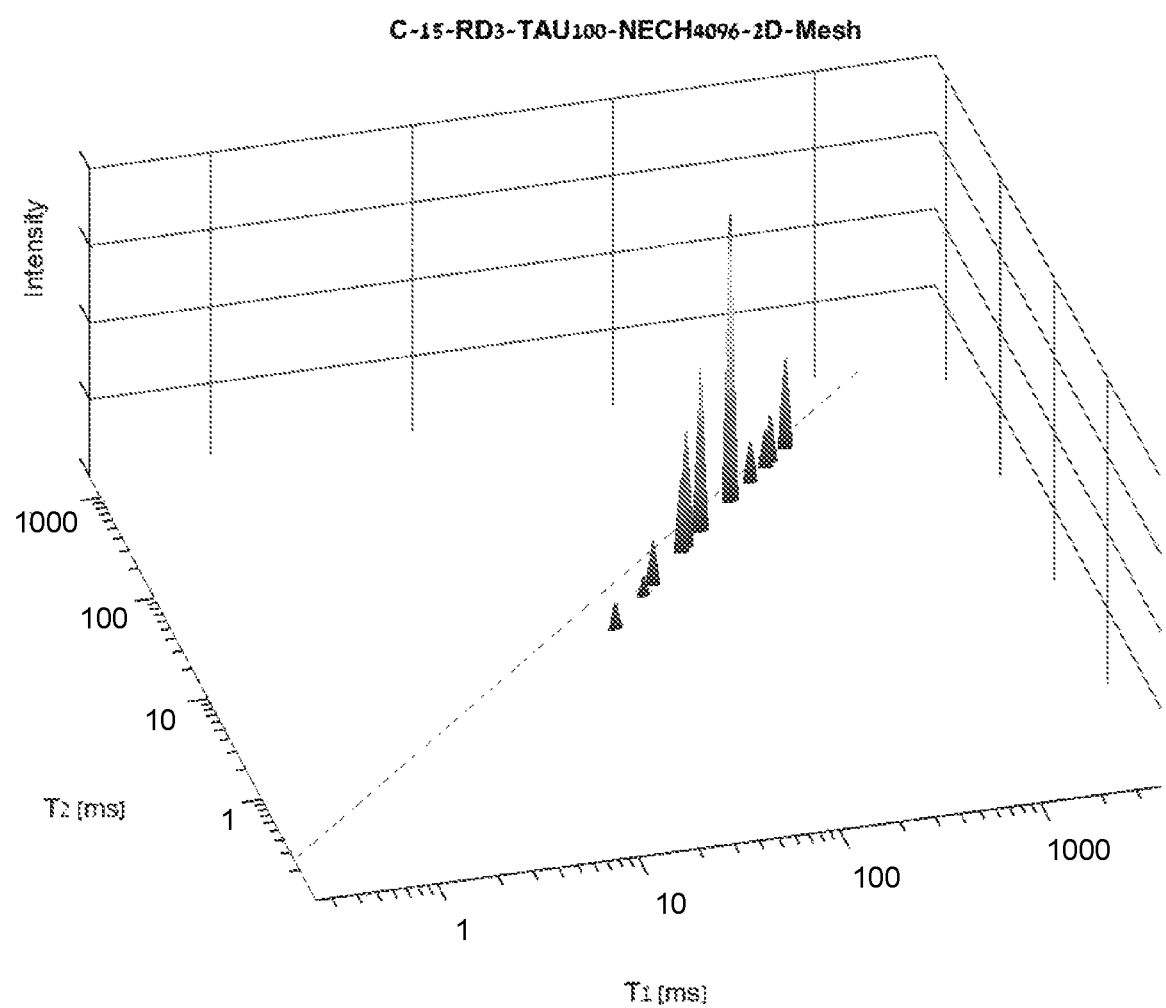
FIGS. 7A and 7B show T1-T2 maps produced for non-oxidized and oxidized samples of pomegranate oil, respectively.
Figure 7B:
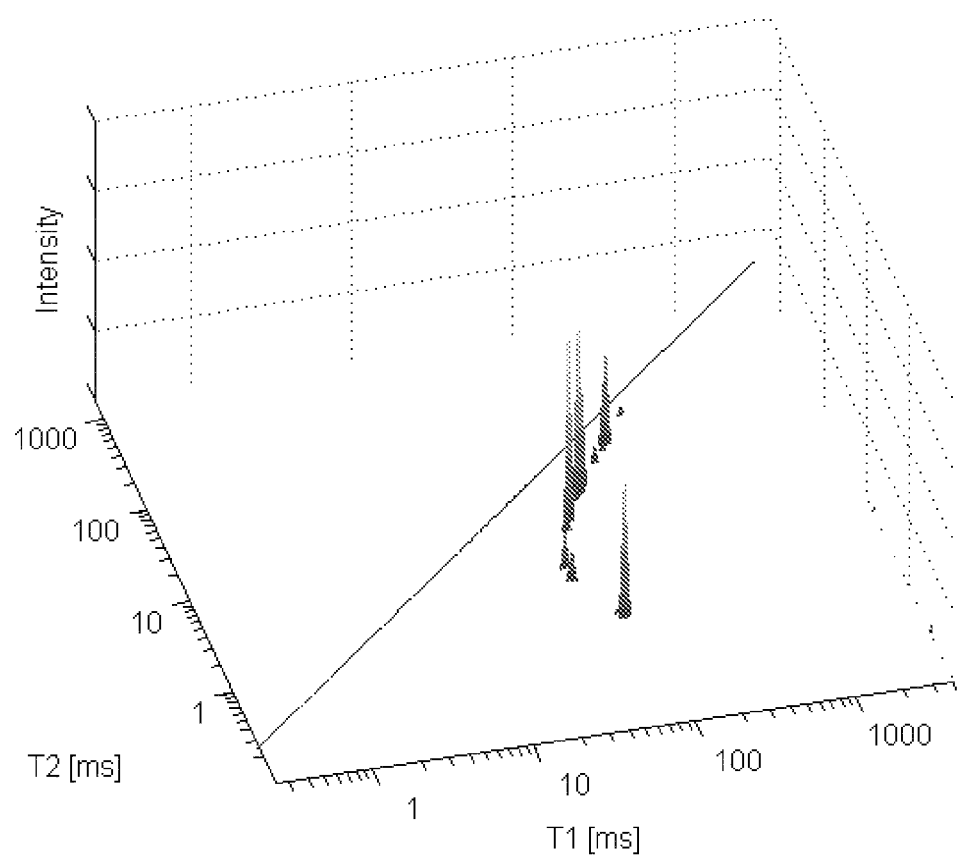

Pomegranate oil is even higher in PUFAs and this fact is confirmed by the greater change in peak movement noted on comparing the maps of FIGS. 7A and 7B.

It is seen that the method of the present invention provides a visually attractive and easy to understand tool for identifying and quantifying the ability of substances to undergo oxidation, by observing changes in peak location and reduction in intensity of starting peaks and generation of new peaks. The individual peaks seen in the maps corresponding to the starting materials (6A, 7A) are due to differences in H1 mobility on different carbons; the new peaks in the maps corresponding to the oxidized samples (6B, 7B) are due to a mixture of molecular oxidized and hydrolyzed products and other oxidized polymerization products.

Figure 6A:
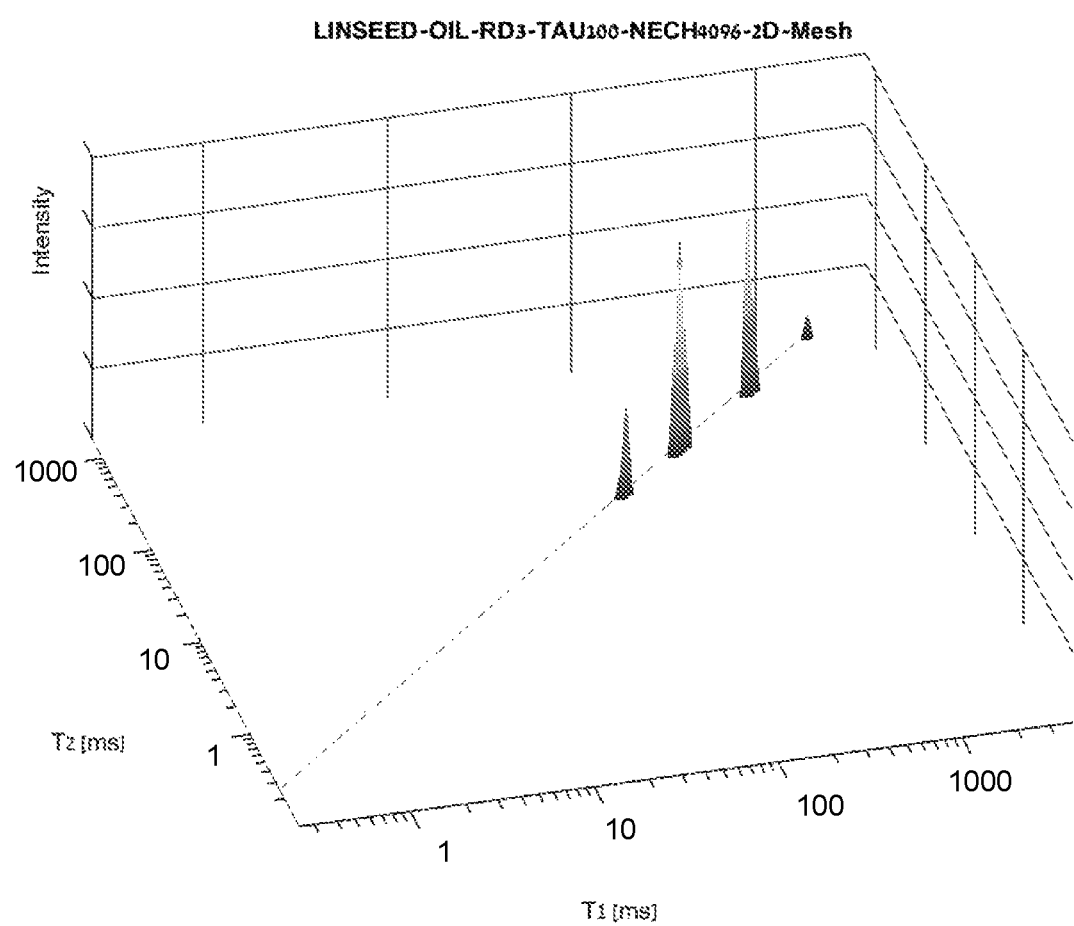
FIGS. 6A to 6C show T1-T2 maps produced for non-oxidized (6A) and oxidized (6B) samples of linseed oil, with FIG. 6C illustrating the effect of tocopherol addition on the oxidation of linseed oil.
Figure 6B:
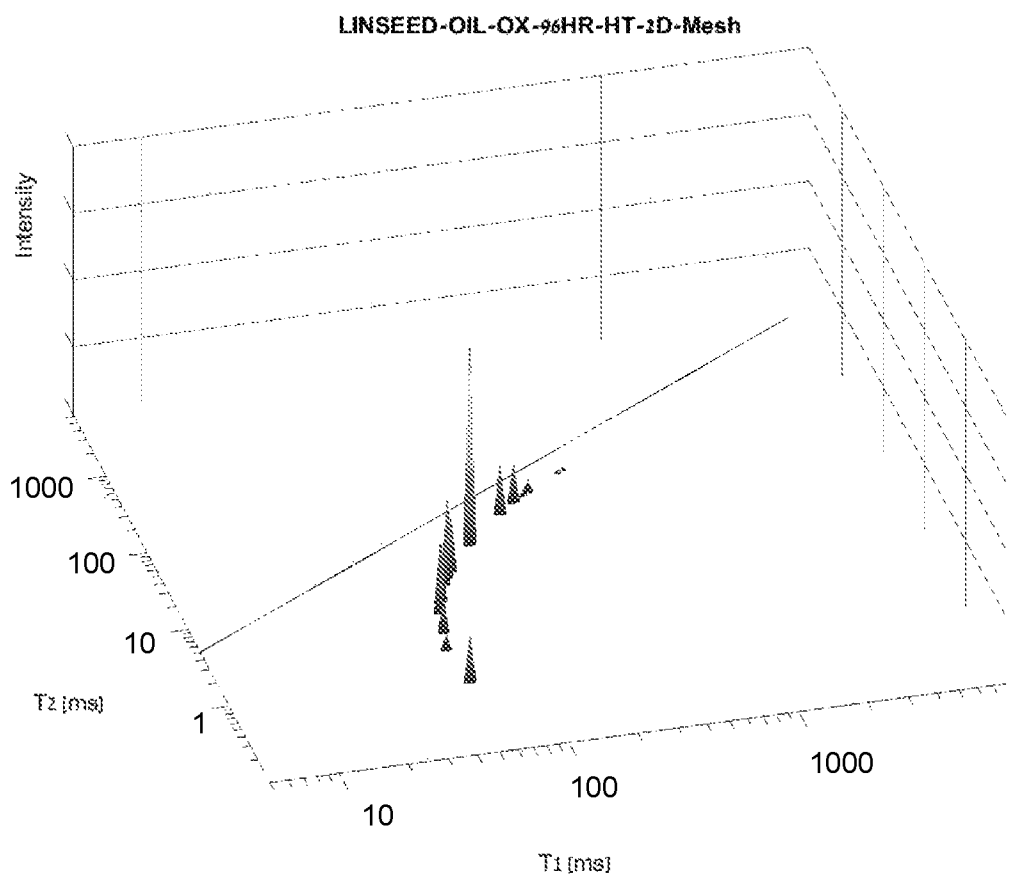
Figure 6C:
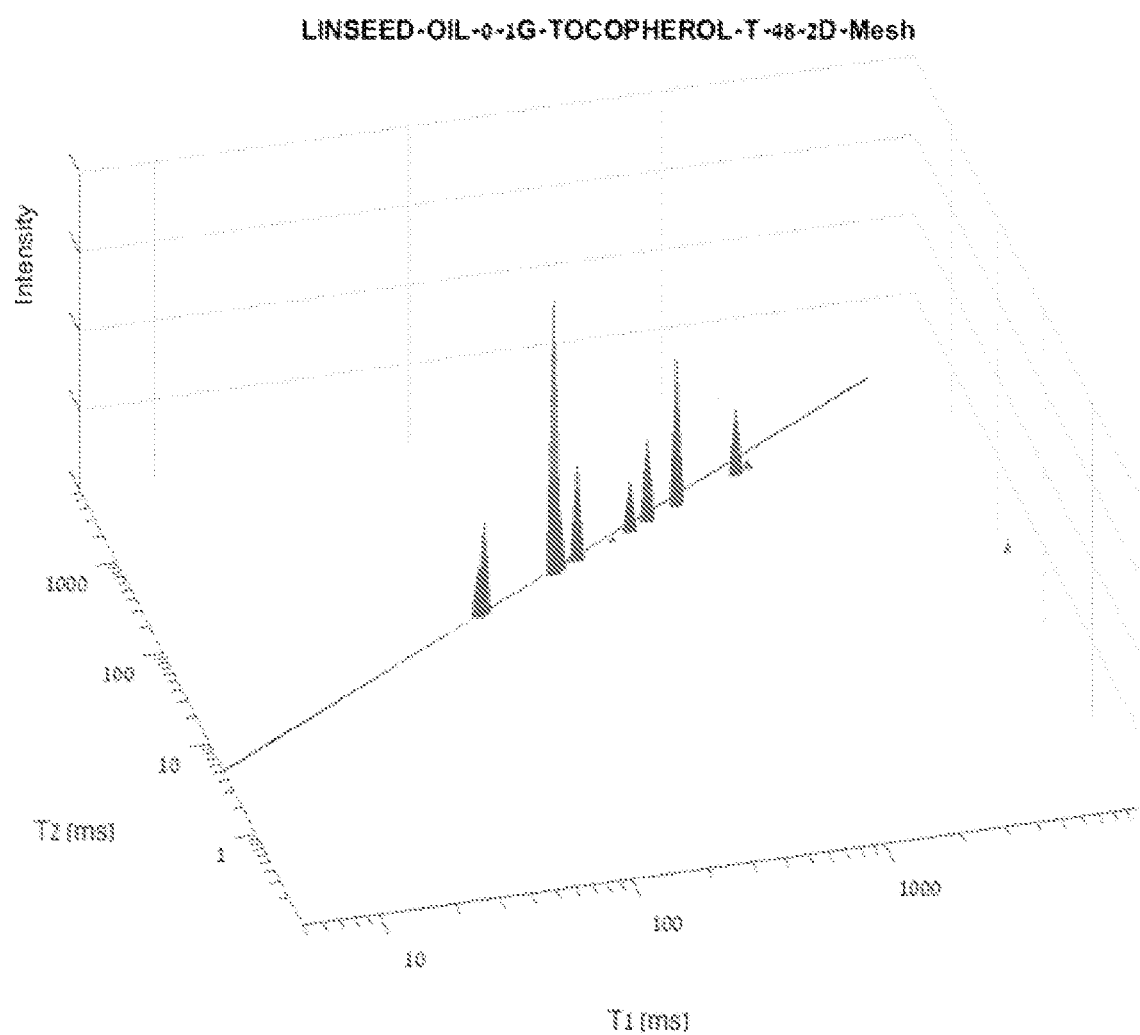

The method of the invention can also be used for the screening of antioxidants by determining the ability of an antioxidant to minimize changes occurring in a 3-D map of a substance subjected to oxidation. That is, a suitable antioxidant should be able to minimize peak shifting, change in peak intensity and new peak generation. For example, as indicated by the 3-D map of FIG. 6C, tocopherol added to linseed oil minimized peak movement or generation of new peaks during oxidation. In this way optimal antioxidants or combinations of antioxidants can be readily identified and the mechanism of efficacy by the peaks affected can be determined. The characteristic peaks seen in the maps of FIGS. 6A, 6B and 6C are tabulated below:

TABLE 6A non heated control linseed oil

| Peak # | T1 (ms) | T2 (ms) | Assignment |
|---|---|---|---|
| 1 | 94 (12%) | 53 (4%) | Glycerol core domain |
| 2 | 191 (45%) | 135 (51%) | Double bond(s) domain |
| 3a | 398 (4%) | 304 (3%) | Head ($C_{1-9}$) aliphatic domain |
| 3b | 437 (21%) | 344 (25%) | |
| 4 | 1003 (18%) | 766 (17%) | Tail ($C_{n-(3-9)}$) aliphatic domain |

TABLE 6B

Oxidized linseed oil after 96 hours of heating.

| Peak # | T1 (ms) | T2 (ms) | Assignment |
|---|---|---|---|
| 1 | 52 | 0.6 | Oxi-polymer aggregate 1 domain |
| 2 | 43 | 1.5 | Oxi-polymer aggregate 2 domain |
| 3 | 45 | 2.5 | Oxi-polymer aggregate 3 domain |
| 4 | 45 | 4.5 | Oxi-polymer aggregate 4 domain |
| 5 | 53 | 8 | Oxi-polymer aggregate 5 domain |
| 6 | 56 | 14 | Oxi-polymer aggregate 6 domain |
| 7 | 70 | 30 | Oxi-polymer aggregate 7 domain |
| 8 | 145 | 48 | Glycerol domain |
| 9 | 190 | 55 | Double bond domain |
| 10 | 225 | 65 | Head ($C_{1-9}$) aliphatic domain |
| 11 | 290 | 245 | Tail ($C_{n-(3-9)}$) aliphatic domain |
| 12 | 305 | 255 | unknown |

TABLE 6C

Oxidized linseed oil with tocopherol after 96 hours of heating

| Peak # | T1 (ms) | T2 (ms) | Assignment |
|---|---|---|---|
| 1 | 85 | 50 | Lipid-glycerol domain |
| 2 | 175 | 120 | Lipid double bond(s) domain |
| 3 | 200 | 180 | Tocopherol aliphatic domain |
| 4 | 320 | 240 | Tocopherol aromatic domain |
| 5a | 390 | 300 | Head ($C_{1-9}$) aliphatic domain |
| 5b | 450 | 350 | |
| 6 | 800 | 580 | Tail ($C_{n-(3-9)}$) aliphatic domain |

As seen in FIGS. 6A, 6B and 6C and the corresponding tabulated data in Tables 6A, 6B, and 6C, the polyunsaturated linolenic oil clearly showed a significant pattern of peak change in the same incubation treatment. Starting from typical four peaks in the control linolenic oil, after 96 hours 11 peaks could be obtained with dramatic shift of most peaks to a lower T1 and T2. Some of the peaks showed a pattern of bending with decreased T2 and constant T1. Interestingly, some peaks showed very minor shift and remain along the diagonal. GC-MS analysis showed a significant reduction in the content of linolenic acid (18:3 PUFA) and a relative increase in the content of oleic acid (18:1). Therefore the most mobile peaks were assigned as non-oxidized oleic acid. Following an intensive orbit-trap MS/M analysis, a group of three peaks was assigned as oxidation aldehyde aggregates. These aldehyde products are known as primary oxidation products of PUFA. The last group of peaks having very short T2 and constant T1 were assigned as oxidation polymeric aggregates (1-4) suggested as secondary and termination oxidation products.

Example 3

Monitoring of Biodiesel Production Process

This example illustrates the application of 1H LF-NMR spectroscopy and signal analysis employing the mathematical method described herein to generate T1-T2 map and enable the monitoring of a process of biodiesel manufacturing. The process involves the transesterification reaction depicted below:

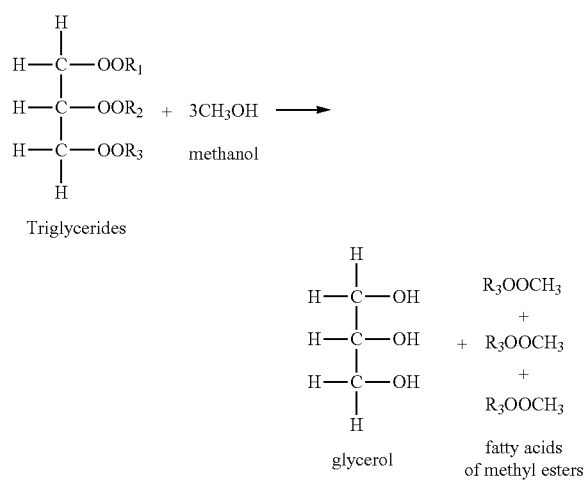

The transesterification reaction was performed with triacyl glycerides mixture (TAG) as the oil, methanol, catalyst, to obtain the final product biodiesel (fatty acids methyl esters—FAME) and glycerin as by-product according to the procedure described by Paula Berman, Adi Leshem, Oren Etziony, Ofer Levi, Yisrael Parmet, Michael Saunders and Zeev Wiesman. Prior to biodiesel production, oils were heated to 80° C. for 1 h to evaporate water, and then allowed to cool down to room temperature. Biodiesels were prepared in a batch laboratory scale TE process with methanol and KOH. Briefly, a potassium hydroxide solution was freshly prepared by mixing methanol (1:6 oil to methanol mol/mol) with KOH (100 g $kg^{-1}$ of the oil). The reaction was carried out for 1 h under reflux at 50° C. with constant stirring and then allowed to cool down to room temperature. The mixture was then transferred to a separating funnel and allowed to stand for approximately 1 h. The bottom layer (glycerol, methanol and most of the catalyst) was drained out. The upper layer (FAMEs, some methanol and traces of the catalyst) was cleaned thoroughly by washing 5 times with warm (~50° C.) de-ionized water. The solution was then heated to 80° C. for 30 min until cleared and left over of water is evaporated.

The characteristic peaks of the original linseed oil and the biodiesel product (after removal of glycerin and before full evaporation of water) are presented in the Tables 7 and 8, respectively. The values are given as average of 5 replicates.

TABLE 7

| Peak # | T1 (ms) | T2 (ms) | Assignment |
|---|---|---|---|
| 1 | 94 | 53 | Glycerol core domain |
| 2 | 191 | 135 | Double bond(s) domain |
| 3a | 398 | 304 | Head ($C_{1-9}$) aliphatic domain |
| 3b | 437 | 344 | |
| 4 | 1003 | 766 | Tail ($C_{n-(3-9)}$) aliphatic domain |

TABLE 8

| Peak # | T1 (ms) | T2 (ms) | Assignment |
|---|---|---|---|
| 1 | 550 | 340 | Double bond(s) domain |
| 2 | 670 | 465 | Head ($C_{1-9}$) aliphatic domain |
| 3 | 810 | 535 | Methylated head domain |
| 4 | 1150 | 755 | Tail ($C_{n-(3-9)}$) aliphatic domain |
| 5 | 3300 | 2250 | Water left over domain |

In addition to characterizing the starting material and the reaction product, the reaction mixture was periodically sampled to generate T1-T2 spectra during progression of the reaction and enable for process monitoring.

Example 4

Monitoring of Product Quality

To demonstrate the efficacy of a 3-D (T1, T2, intensity) map generated by the method of the invention in monitoring the quality of products, a library of various products was compounded. Another important aspect of the present invention is the identification of chemical sites of the tested materials, which can then be placed within a "material dictionary" for a reference. Such sites include chemical sites on lipids or aliphatic chains such as $^1$H attached to the head groups of fatty acids, to glycerol moieties of lipids, or to a single or multiple double bond(s) in an unsaturated portion of the aliphatic chains. Various lipids and oils and other materials can thus be characterized with respect to variations in their chemical structures such as the different amounts of double bonds in the aliphatic chains and different head groups, stereo chemical arrangements. As shown below, this can also be used to readily monitor chemical changes in the identified groups under stressed stability testing conditions or oxidation conditions. This example shows how a wide variety of materials can be readily characterized, ranging from relatively simple lipids such as fatty acids and complex oils' mixtures such as linseed oils and rapeseed oil, food materials based on complex emulsions such as mayonnaise and butter, and natural biological materials such as lentils, chickpea (hummus), fenugreek, and castor seed, and even living systems such as red microalgae.

Octanoic, decanoic, palmitoleic, oleic, linoleic, alpha-linoleic and erucic acids, as well as linseed oil, rapeseed oil, and soybean oil (all by Sigma Aldrich 99.9%) were measured using LF-NMR as described in previous example. The obtained relaxation data were processed using the PDCO routine based on $L_1$ and $L_2$ regularization as described herein, to generate the 3D maps of T1, T2 and the intensity.

In addition to the spectroscopic graph, a segmental and environmental motion characterization of the tested samples, completed with table presenting the T1 and T2 values is set out herein. All these are used for generation of a chemical morphological dictionary (chemorphology) dictionary of the tested samples.

The characteristic peaks are presented in Table 9 below (values are given as average of 5 replicates).

TABLE 9

| Material name | Peak # | T1 (ms) | T2 (ms) | Assignment |
|---|---|---|---|---|
| Octanoic acid | 1 | 722 | 691 | Head to head domain |
| (C8:0) | 2 | 835 | 84 | Aliphatic chain domain |
| Decanoic acid | 1 | 363 | 335 | Head to head domain |
| (C10:0) | 2 | 586 | 543 | Aliphatic chain domain |
| Palmitoleic acid | 1 | 195 | 190 | Head to head domain |
| (C16:1, cis 9) | 2 | 205 | 203 | Double bond domain |
|  | 3 | 447 | 423 | Head aliphatic domain |
|  | 4 | 740 | 666 | Tail aliphatic domain |
| Oleic acid | 1 | 160 | 153 | Head to head domain |
| (C18:1, cis 9) | 2 | 181 | 174 | Double bond domain |
|  | 3 | 281 | 277 | Head aliphatic domain |
|  | 4 | 633 | 544 | Tail aliphatic domain |
| Linoleic acid | 1 | 320 | 291 | Head to head domain |
| (C18:2, cis 9, 12) | 2 | 845 | 695 | Double bond domain |
|  | 3 | 1122 | 852 | Head aliphatic domain |
|  | 4 | 1217 | 950 | Tail aliphatic domain |
| Alpha-linoleic acid | 1 | 309 | 302 | Head to head domain |
| (C18:3 cis 9, 12, 15) | 2 | 442 | 444 | Double bond domain |
|  | 3 | 1099 | 927 | Head aliphatic domain |
|  | 4 | 2260 | 1948 | Tail aliphatic domain |
| Erucic acid | 1 | 120 | 102 | Head to head domain |
| (22:1, cis 13) | 2 | 159 | 141 | Double bond domain |
|  | 3 | 192 | 166 | Head aliphatic domain |
|  | 4 | 431 | 399 | Tail aliphatic domain |

It is known that fatty acids in the liquid phase are assembled in head-to-head dimers. The carboxyl-carboxyl interaction is thus highly stabilized. Therefore, for saturated acids, two domains can be discerned. The more stable head is assigned to domain 1. The aliphatic chains of the relatively short fatty acid are partially stabilized with hydrogen bonds, and are assigned to domain 2. Similar explanations go for decanoic acid as for octanoic acid. However the T1 and T2 values are shorter than in the previous case due to increased number of hydrogen bonds.

For unsaturated acids further domains are discerned. As for each fatty acid a domain of the dimer head to head is obtained at the less mobile part of the spectrum map. The second domain is that of the double bond segment that is known to have a low mobility. The domain of the aliphatic chain from the head of the chain up to the double bond that is stabilized with hydrogen bonds along this 9 carbon chain has relatively longer T1-T2 value. The domain of the tail is the longest relaxation time value due to relatively higher degree of freedom. Palmitoleic and oleic acid show similar patterns; however, the T1-T2 values are shorter due to the additional two carbons in the oleic acid. For linoleic acid, the pattern is similar to other acids. However, the T1-T2 values are longer in comparison to oleic acid due to the additional double bond and the shorter tail in the linoleic acid that affects the internal environment and packaging. A similar pattern is observed for other fatty acids.

Linseed oil had the following composition of fatty acids: (16:0)—5%, (16:1)—1%, (18:0)—4%, (18:1)—20%, (18:2)—15%, (18:3)—55%.

The characteristic peaks are presented in Table 10 below. The values are given as average of 5 replicates.

TABLE 10

| Peak # | T1 (ms) | T2 (ms) | Assignment |
|---|---|---|---|
| 1 | 94 (12%) | 53 (4%) | Glycerol core domain |
| 2 | 191 (45%) | 135 (51%) | Double bond(s) domain |
| 3a | 398 (4%) | 304 (3%) | Head ($C_{1-9}$) aliphatic domain |
| 3b | 437 (21%) | 344 (25%) | |
| 4 | 1003 (18%) | 766 (17%) | Tail ($C_{n-(3-9)}$) aliphatic domain |

It is known that the core glycerol moiety of triacylglycerols is highly stabilized and is considered as the less mobile segment. Therefore it is assigned to domain 1. The double bond segment is also relatively less mobile and assigned to domain 2. The aliphatic chain from the head up to the double bond(s) segment is relatively more mobile and assigned to domain 3. The short aliphatic chain of the tail is considered the most mobile segment and assigned to domain 4.

Spectra were likewise generated for rapeseed oil and soybean oil. The rapeseed oil spectrum exhibits peaks at T1-T2: 55-30; 110-85; 190-150; 220-170; 310-250 for peaks 1;2;3a;3b;4, respectively. The soybean oil spectrum exhibits peaks at T1-T2: 50-30; 95-65; 160-110; 180-120; 245-190 for peaks 1;2;3a;3b;4, respectively, both oils in line with the observations made for linseed oil.

Additionally, several solid products were tested using LF-NMR. Castor seeds (Ricinuscommunis), chickpeas seeds (*Cicer arietinum, Alias hummus*), lentils seeds (*Lens culinaris*), fenugreek (trigonellafoenumgraekum), or dried powder of red microalgae (Porphyridiumcruentum). ca 5 g of either product, were placed into test tubes and analyzed in LF-NMR as described above. The obtained relaxation data was processed as described above.

The 2D T1-T2 map of chickpea seeds demonstrates the 4 typical domains of oils. Another significant big peak (domain 5) that was obtained in T1-T2 relaxation time value corresponds to starch. The characteristic peaks of chickpeas seeds are presented in table 11 below. The values are given as average of 5 replicates.

TABLE 11

| Peak # | T1 (ms) | T2 (ms) | Assignment |
|---|---|---|---|
| 1 | 55 (3%) | 45 (4%) | Glycerol core domain |
| 2 | 65 (30%) | 60 (27%) | Double bond(s) domain |
| 3a | 175 (26%) | 125 (25%) | Head ($C_{1-9}$) aliphatic domain |
| 3b | 207 (1%) | 172 (1%) | |

TABLE 11-continued

| Peak # | T1 (ms) | T2 (ms) | Assignment |
|---|---|---|---|
| 4 | 375 (4%) | 295 (6%) | Tail ($C_{n-(3-9)}$) aliphatic domain |
| 5 | 85 (34%) | 0.8 (37%) | Starch domain |

The characteristic peaks of lentils seeds are presented in Table 12 below (values are given as average of 5 replicates).

TABLE 12

| Peak # | T1 (ms) | T2 (ms) | Assignment |
|---|---|---|---|
| 1 | 100 (72%) | 0.5 (71%) | Starch aggregate domain |
| 2 | 100 (4%) | 1.3 (3%) | Glycerol core domain |
| 3a | 100 (1%) | 6 (2%) | Double bond(s) domain |
| 4 | 130 (14%) | 70 (15%) | Head ($C_{1-9}$) aliphatic domain |
| 5 | 220 (3%) | 90 (10%) | Tail ($C_{n-(3-9)}$) aliphatic domain |

The characteristic peaks of fenugreek seeds are presented in Table 13 below (values are given as average of 5 replicates).

TABLE 13

| Peak # | T1 (ms) | T2 (ms) | Assignment |
|---|---|---|---|
| 1 | 19 (1%) | 2.5 (3%) | Oxi aggregate domain |
| 2 | 24 (13%) | 14 (15%) | Glycerol core domain |
| 3a | 60 (46%) | 25 (44%) | Double bond(s) domain |
| 4 | 115 (24%) | 70 (25%) | Head ($C_{1-9}$) aliphatic domain |
| 5 | 210 (16%) | 130 (13%) | Tail ($C_{n-(3-9)}$) aliphatic domain |

The characteristic peaks of castor seeds are presented in Table 14 below (values are given as average of 5 replicates).

TABLE 14

| Peak # | T1 (ms) | T2 (ms) | Assignment |
|---|---|---|---|
| 1 | 19 (1%) | 2.5 (3%) | Oxi aggregate domain |
| 2 | 24 (13%) | 14 (15%) | Glycerol core domain |
| 3a | 60 (46%) | 25 (44%) | Double bond(s) domain |
| 4 | 115 (24%) | 70 (25%) | Head ($C_{1-9}$) aliphatic domain |
| 5 | 210 (16%) | 130 (13%) | Tail ($C_{n-(3-9)}$) aliphatic domain |

The characteristic peaks of *Cicer arietinum* seeds are presented in the Table 15 below (values are given as average of 5 replicates).

TABLE 15

| Peak # | T1 (ms) | T2 (ms) | Assignment |
|---|---|---|---|
| 1 | 100 (31%) | 0.5 (32%) | Starch aggregate domain |
| 2 | 100 (1%) | 6 (1%) | Unknown |
| 3 | 90 (8%) | 60 (7%) | Glycerol domain |
| 4 | 140 (24%) | 80 (25%) | Double bond(s) domain |
| 5a | 220 (26%) | 140 (24%) | Head ($C_{1-9}$) aliphatic domain |
| 5b | 245 (3%) | 165 (3%) | Head ($C_{1-9}$) aliphatic domain |
| 6 | 460 (7%) | 300 (8%) | Tail ($C_{n-(3-9)}$) aliphatic domain |

The 2D T1-T2 map of dry powder of red microalgae (*Porphyridium* sp.) demonstrates oil peaks along the diagonal (T1 range of 100-400 ms and T2 range of 80-200 ms). A major peak (T1~40 ms and T2~0.6 ms) typical of polysaccharides was assigned as sulfated polysaccharides—a well-known main component of this red algae strain. Another peak (domain 4, 105;6) was assigned as amorphous polysaccharides, corresponding to a standard test. Three crystalline cellulose fibers' peaks (domains 1 and 2, 1;0.4, 10;0.4, and 13;0.4), were assigned by standard tests (see Example 1). The characteristic peaks are presented in table 16 below (values are given as average of 5 replicates).

TABLE 16

| Peak # | T1 (ms) | T2 (ms) | Assignment |
|---|---|---|---|
| 1 | 1 | 0.4 | Cellulose, crystalline |
| 2a | 10 | 0.4 | Cellulose, semi-crystalline A |
| 2b | 13 | 0.4 | Cellulose, semi-crystalline B |
| 3 | 30 | 0.5 | Sulfated polysaccharides |
| 4 | 105 | 6 | Amorphous polysaccharides |
| 5 | 65 | 9 | Unknown |
| 6 | 80 | 35 | Lipid double bond(s) domain |
| 7 | 120 | 75 | Lipid aliphatic head domain |
| 8 | 280 | 190 | Lipid aliphatic tail domain |
| 9 | 1850 | 90 | Sulfated surfactant |
| 10 | 2250 | 850 | Water residues |

Further complex materials were represented by mayonnaise. The product (Heinz mayonnaise) was tested as above.

The 2D T1-T2 map of mayonnaise emulsion demonstrates typical oil peaks along the diagonal. Following standard tests, additional two peaks (domains 5 and 6, at 750;650, and 4000;550) differing with T1 time values and similar T2 times were assigned as lecithin aggregated populations (a and b). Another very mobile peak (4500;4000) was assigned as water based on T1 and T2 time values. The characteristic peaks are presented in Table 17 below (values are given as average of 5 replicates).

TABLE 17

| Peak # | T1 (ms) | T2 (ms) | Assignment |
|---|---|---|---|
| 1 | 35 | 30 | Lipid-glycerol domain |
| 2a | 70 | 60 | Lipid double bond(s) domain |
| 2b | 80 | 70 | |
| 3 | 200 | 190 | Lipid aliphatic head domain |
| 4 | 450 | 380 | Lipid aliphatic tail domain |
| 5 | 750 | 650 | Lecithin aggregates domain |
| 6 | 4000 | 550 | |
| 7 | 4500 | 4000 | Water |

The results show that a qualitative and quantitative fingerprint of the products may be readily obtained by the techniques disclosed herein.

Example 5

Monitoring of Oxidation of Oil, Biodiesel and Food Products

To demonstrate the efficacy of a 3D (T1, T2, intensity) map generated by the method of the invention in investigating oxidation processes of various materials, rapeseed oil, soybean oil, bovine cream butter and linseed biodiesel were separately oxidized at 80° C. with bubbling of air through the sample over 24, 48, 72, 96 hours. The 3-D maps were created by obtaining the NMR relaxation times measurements and using the computational procedure described herein. Characteristic peaks are tabulated below for each of the tested materials, before the heating and after the 96 hours heating period.

TABLE 18

Bovine cream butter (control, non heated)

| Peak # | T1 (ms) | T2 (ms) | Assignment |
|---|---|---|---|
| 1 | 55 | 40 | Glycerol core domain |
| 2 | 80 | 60 | Double bonds domain |
| 3 | 255 | 170 | Aliphatic chain from head (9 carbons) |
| 4 | 290 | 165 | Aliphatic chain of tail (carbons) domain |

TABLE 19

Bovine cream butter (96 hours heated butter)

| Peak # | T1 (ms) | T2 (ms) | Assignment |
|---|---|---|---|
| 1 | 50 | 35 | Glycerol core domain |
| 2 | 105 | 70 | Double bonds domain |
| 3 | 195 | 125 | Aliphatic chain from head (9 carbons) |
| 4 | 265 | 180 | Aliphatic chain of tail (carbons) domain |

The T1-T2 map of saturated fat of bovine cream butter showed that it was not oxidized after 96 hours of incubation in 80° C.

TABLE 20 rapeseed oil (control, non heated)

| Peak # | T1 (ms) | T2 (ms) | Assignment |
|---|---|---|---|
| 1 | 55 | 30 | Glycerol core domain |
| 2 | 110 | 85 | Double bonds domain |
| 3a | 190 | 150 | Aliphatic chain from head (9 carbons) |
| 3b | 220 | 170 | Aliphatic chain from head (9 carbons) |
| 4 | 310 | 250 | Aliphatic chain of tail (carbons) domain |

TABLE 21 rapeseed oil (96 hours heated rapeseed oil)

| Peak # | T1 (ms) | T2 (ms) | Assignment |
|---|---|---|---|
| 1 | 25 | 4 | Oxi aggregate domain |
| 2 | 30 | 10 | Secondary oxy-aldehyde 1 domain |
| 3 | 39 | 21 | Secondary oxy-aldehyde 2 domain |
| 4 | 70 | 50 | Glycerol core domain |
| 5 | 110 | 80 | Aliphatic chain from head (9 carbons) |
| 6 | 190 | 140 | Aliphatic chain from head (9 carbons) |
| 7 | 260 | 190 | Aliphatic chain of tail (carbons) domain |

The T1-T2 map of monounsaturated oil of rapeseed showed that it was only slightly oxidized after 96 hours of incubation in 80° C.

TABLE 22 soybean oil (control, non heated)

| Peak # | T1 (ms) | T2 (ms) | Assignment |
|---|---|---|---|
| 1 | 50 | 30 | Glycerol core domain |
| 2 | 95 | 65 | Double bonds domain |
| 3a | 160 | 110 | Aliphatic chain from head (9 carbons) |
| 3b | 180 | 120 | Aliphatic chain from head (9 carbons) |
| 4 | 245 | 190 | Aliphatic chain of tail (carbons) domain |

TABLE 23 soybean oil (96 hours heated soy oil)

| Peak # | T1 (ms) | T2 (ms) | Assignment |
|---|---|---|---|
| 1 | 23 | 3 | Oxi. polymer aggregate domain |
| 2 | 23 | 5 | Oxi. polymer aggregate domain |
| 3 | 31 | 8 | Secondary oxy-aldehyde 1 domain |
| 4 | 40 | 30 | Secondary oxy-aldehyde 2 domain |
| 5 | 50 | 40 | Glycerol core domain |
| 6 | 65 | 50 | Unknown |
| 7 | 85 | 65 | Double bond domain |
| 8a | 110 | 90 | Aliphatic chain from head (9 carbons) |
| 8b | 170 | 130 | Aliphatic chain from head (9 carbons) |
| 9 | 220 | 170 | Aliphatic chain of tail (carbons) domain |

The T1-T2 map of di-unsaturated oil of soy showed that it tended to oxidize after 96 hours of incubation in 80° C. more than the rapeseed monounsaturated oil.

TABLE 24 linseed oil biodiesel (control, non heated)

| Peak # | T1 (ms) | T2 (ms) | Assignment |
|---|---|---|---|
| 1 | 550 | 340 | Double bond (s) domain |
| 2 | 670 | 465 | Head ($C_{1-9}$) aliphatic domain |
| 3 | 810 | 535 | Methylated head domain |
| 4 | 1150 | 755 | Tail ($C_{n-(3-9)}$) aliphatic domain |
| 5 | 3300 | 2250 | Residue of non evaporated water and methanol |

TABLE 25 linseed oil biodiesel (96 hours heated linseed oil biodiesel)

| Peak # | T1 (ms) | T2 (ms) | Assignment |
|---|---|---|---|
| 1 | 33 | 7 | Aldehydes aggregate 1 domain |
| 2 | 42 | 21 | Aldehydes aggregate 2 domain |
| 3 | 59 | 50 | Aldehydes aggregate 3 domain |
| 4 | 98 | 87 | Double bind(s) domain of non oxidized domain of monounsaturated FAME (Oleic) |
| 5 | 175 | 140 | Head ($C_{1-9}$) aliphatic non oxidized domain of monounsaturated FAME (Oleic) |
| 6 | 360 | 235 | Methylated head domain of monounsaturated FAME (Oleic) |
| 7 | 395 | 310 | Tails of non oxidized domain of monounsaturated FAME (Oleic) |

The results show that linseed biodiesel oxidation can be monitored by the method of the invention.

Example 6

Computational Procedures—PDCO $L_1/L_2$ Routine and $L_2$ Routine

PDCO is freely available Matlab optimization routine found at https://github.com/mxsaunders/pdco.

Documentation of the PDCO routines and its usage is available at: https://github.com/mxsaunders/pdco/blob/master/doc/notes07-PDinterior.pdf The main optimization routine is pdco.m, which solves the following optimization problem:

$$\min_{x,r} \varphi(x) + \frac{1}{2}\|D_1 x\|_2^2 + \frac{1}{2}\|r\|_2^2 \quad (4)$$

$$\text{s.t. } Ax + D_2 r = b$$

$$l \leq x \leq u,$$

Where x,r are the decision variables vectors, $\varphi(x)$ is a convex function and D1,D2 are positive diagonal matrices. The matrix A can be defined either as a standard matrix or as an operator Matlab function as explained below.

The Matlab command for running pdco is:

$$x = pdco(pdObj, pdMat, b, bl, bu, d1, d2, \text{options}, x0, y0, z0, \text{xsize}, \text{zsize})$$

where the input variables are the following:

pdObj—a function that evaluates $\varphi(x)$. If $\varphi(x)$ is a linear function, as in the present case, it is possible to replace it with an input vector c, in which case $\varphi(x) = c^T x$ pdMat—the matrix A in equation (4)

b—The right-hand side vector of the constraints in (4)

bl,bu—real vectors representing the lower and upper limits l and u in (4)

d1,d2—real positive vectors representing the diagonal elements of the matrices D1 and D2 in (4)

options—A Matlab structure that stores various tuning parameters of the PDCO algorithm; it can be created using the Matlab function pdcoSet.m x0,y0,z0—vectors with initial values for the decision and dual variables xsize, zsize—scalars that estimates the magnitude of the primal and dual variables.

In order to "feed" the minimization problem to the PDCO routine, the following matrices and vectors definitions should be made:

$$\varphi(x) = \lambda_1 \|c\| = \lambda_1 \sum_j \{(c_1)_j + (c_2)_j\}, \quad (4)$$

$$A = \begin{pmatrix} K & 0 & 0 \\ -I & B & -B \end{pmatrix}, D_1 = \begin{pmatrix} \delta_1 I & & \\ & \sqrt{\lambda_2} I & \\ & & \sqrt{\lambda_2} I \end{pmatrix}, D_2 = \begin{pmatrix} I & & \\ & \delta_1 I & \\ & & \delta_1 I \end{pmatrix},$$

$$l = \begin{pmatrix} 0 \\ 0 \\ 0 \end{pmatrix}, u = \begin{pmatrix} \infty \\ \infty \\ \infty \end{pmatrix}, x = \begin{pmatrix} f \\ c_1 \\ c_2 \end{pmatrix}, r = \begin{pmatrix} r_1 \\ r_2 \end{pmatrix}, b = \begin{pmatrix} s \\ 0 \end{pmatrix}.$$

where $\delta_1$ and $\delta_2$ are small positive values (can be anywhere in the range 1e-6 to 1e-12 for example) and c1 and c2 are the positive and negative parts of c respectively such that c=c1−c2. Replacing c by the difference of c1 and c2 is needed in order to represent the sum of absolute values of the components of c (the l1 norm) as a linear sum, which is a convex function in the weak sense so that the convexity requirement of $\varphi(x)$ is satisfied.

For simplicity we use a trivial dictionary B=I, where I is the identity matrix representing the elementary basis. Then (4) is reduced to the following form:

$$\varphi(x) = \lambda_1 \|f\| = \lambda_1 \Sigma f_j,$$

$$A = K, D_1 = \sqrt{\lambda_2} I, D_2 = I,$$

$$l = 0, u = \infty, x = f, b = s, \quad (5)$$

The main reason for the simplification in this case is the fact that the sum of absolute values of the components of f becomes a regular sum because the elements of f are all positive.

Although it is possible to construct a very large matrix K and use it as an input for the PDCO routine, it is much more efficient, computation time wise as well as storage wise, to define A as a linear operator Matlab function that applies K to f equivalently by first arranging f as a matrix F and then apply the much smaller $K_1$ and $K_2$ matrices from the left and right as presented in (1).

In order to define A as an operator in matlab, it must be defined as a Matlab handle to a function via A=@Aprod, where Aprod.m is the following Matlab function:

```
function y = Aprod (mode,m,n,F)
global K1,K2
n1=size(K1,2);
m2=size(K2,1);
if mode == 1, % Forward operator
F=reshape(F(:),n1,n2);
    y=K1*F*K2;
else %Adjoint operator
    F=reshape(F(:),n1,n2);
y=K1'*F*K2';
end
    y=y(:);
```

The matrices $K_1$ and $K_2$ are global variables that are built using separate Matlab routines. mode, m, n and F are inputs that are sent by PDCO.m.

Example 7

Validation

In order to validate the 2D reconstruction as described herein, e.g. with PDCO, we generated simulated 2D spectrums with three spiky peaks by taking a zero matrix $F_{120,512}$ (matrix of zeros of dimensions 120 and 512) for the T1 and T2 relaxation rates respectively and then placing intensity values of 5000 at the peaks locations. The peaks were either 1) located on the T1/T2 diagonal, 2) located about the diagonal, and 3) two peaks on the diagonal with the third being below the diagonal. The corresponding relaxation signal was simulated using the 2D discrete Laplace transformation of the matrix F, to obtain the 2D simulated relaxation matrix S. To get the reconstructed 2D spectrum the PDCO routine was applied to solve the optimization problem (1) where F is the resulting 2D reconstructed spectrum, B=I, R is the residuals matrix and f and r are the vector representation of the matrices F and R respectively.

Figure 8A:
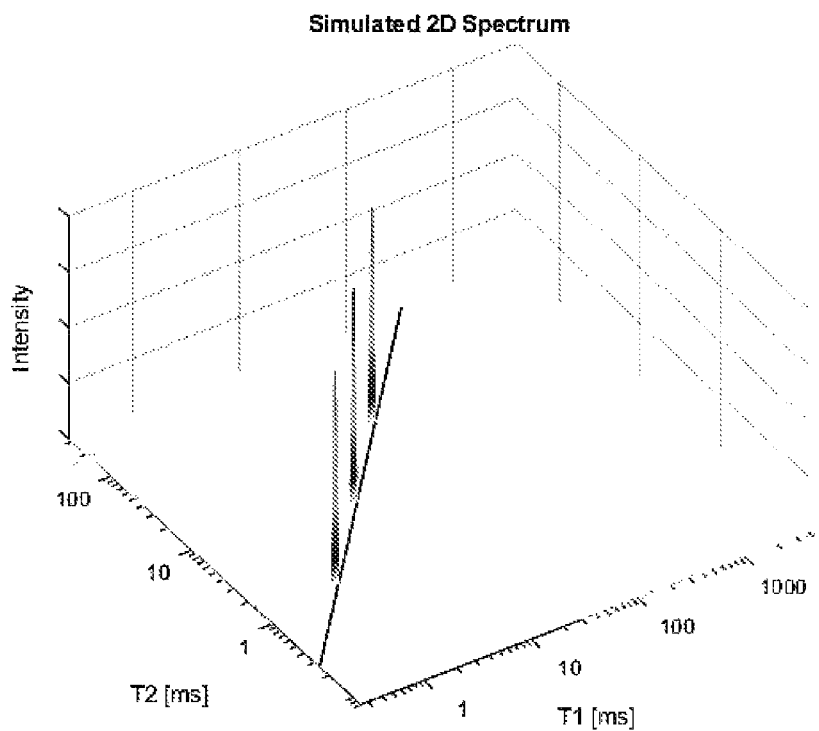
FIGS. 8A and 8B compare between original simulated 2D spectrums and their corresponding reconstruction.
Figure 8B:
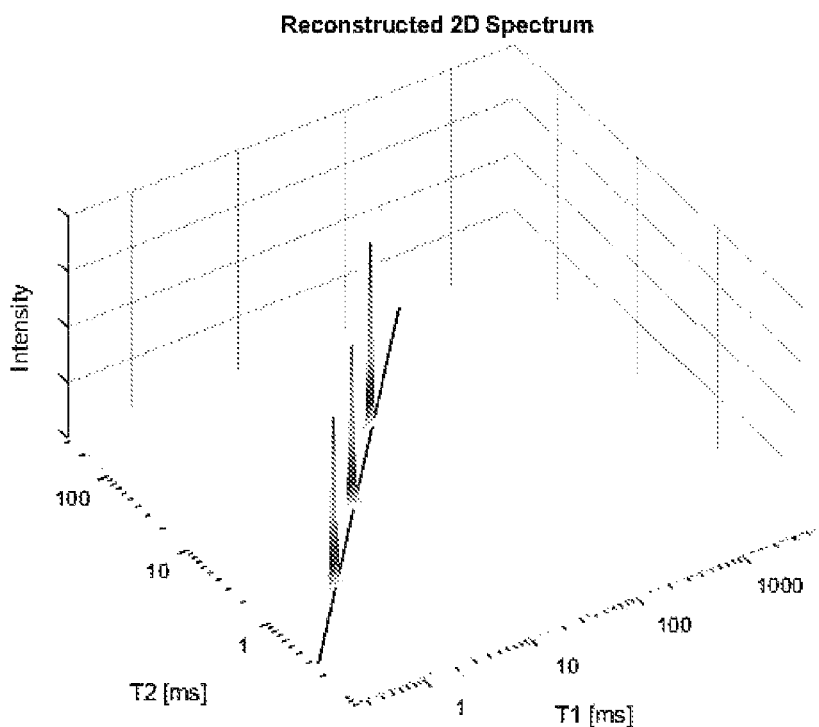
Figure 9A:
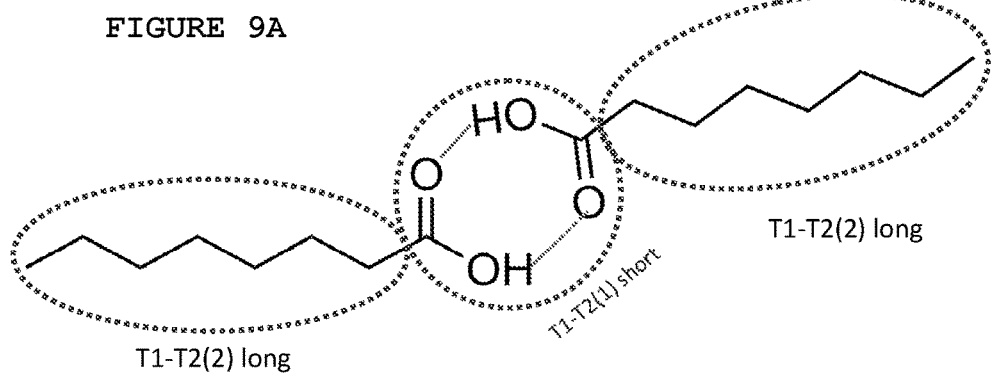
FIGS. 9A to 9G depict the structures of fatty acids which were resolved with the aid of the method of the invention: Octanoic acid (C8:0); Decanoic acid (C10:0); Palmitoleic acid (C16:1, cis 9); Oleic acid (C18:1, cis 9); Linoleic acid (C18:2, cis 9,12); Alpha Linolenic acid (C18:3 cis 9,12,15); and Erucic acid (22:1, cis 13).
Figure 9B:
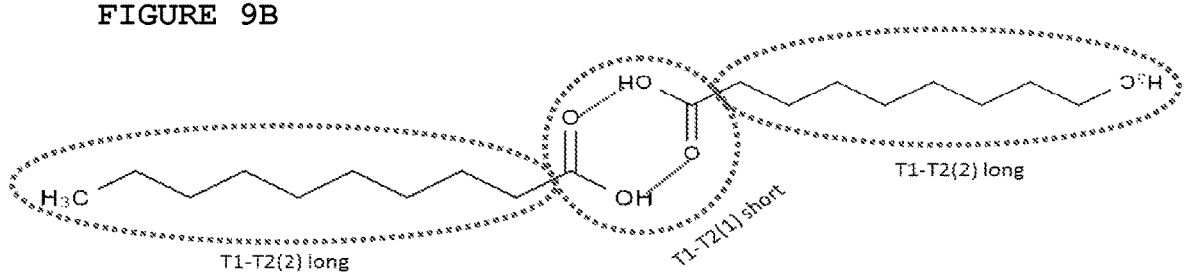
Figure 9C:
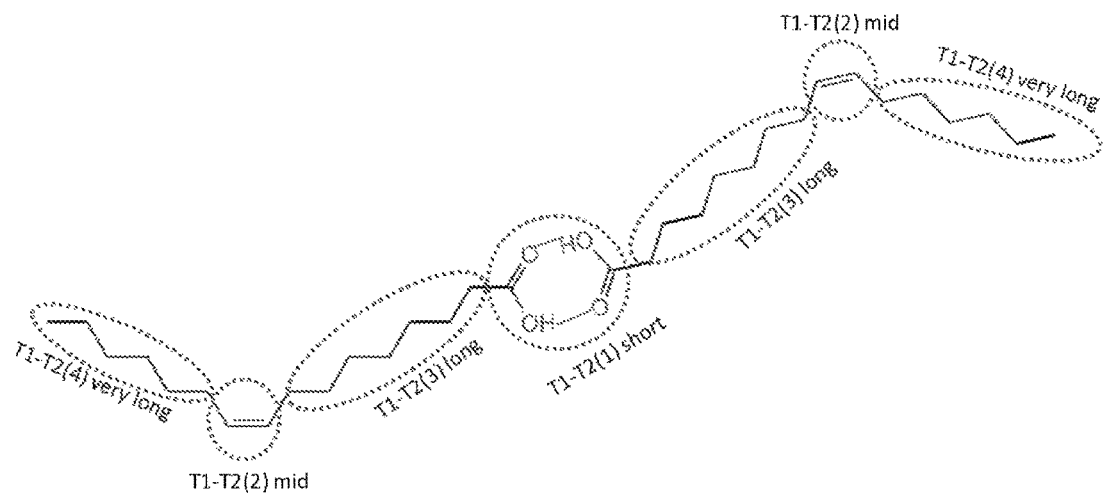
Figure 9D:
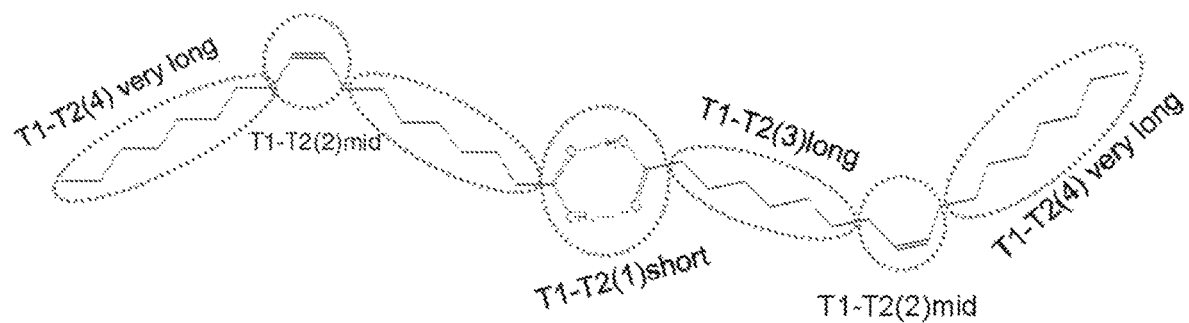
Figure 9E:
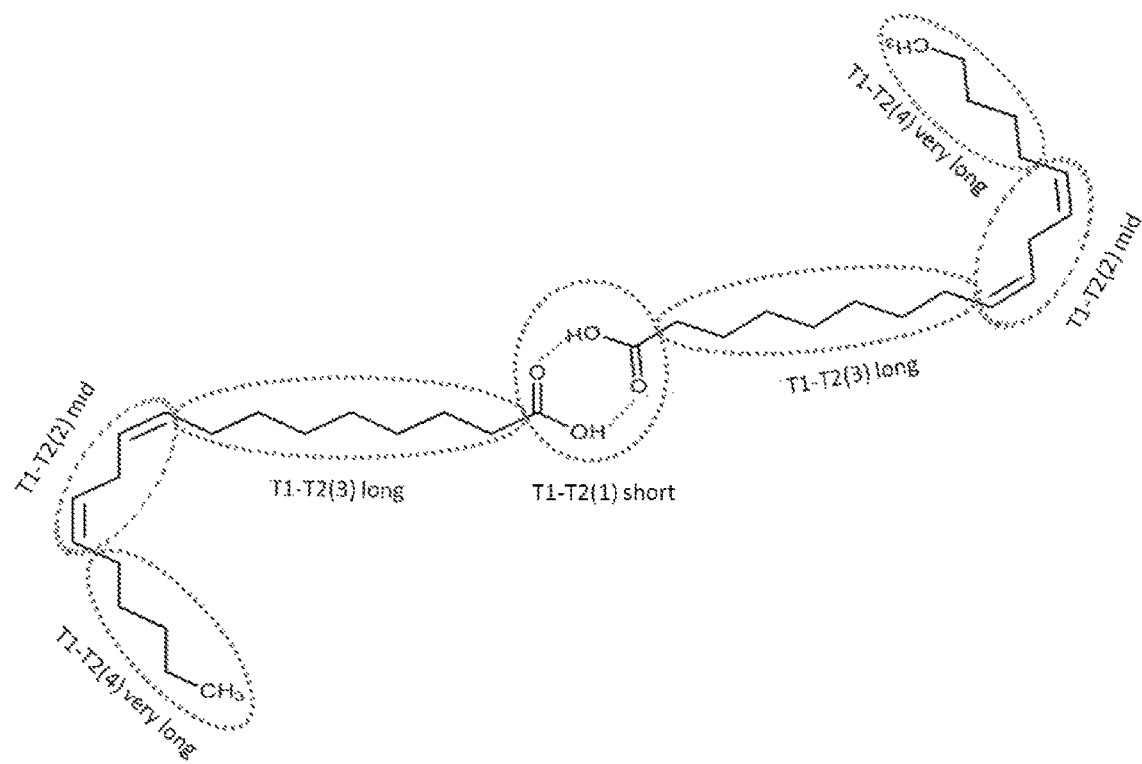
Figure 9F:
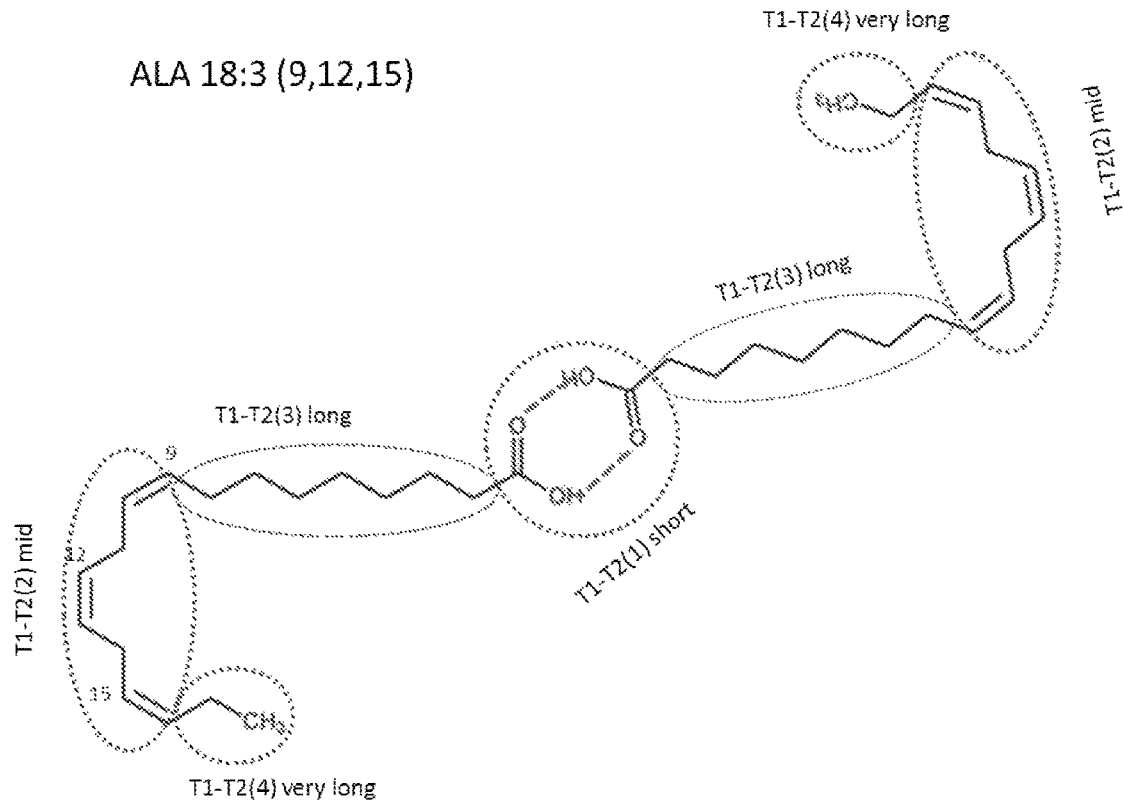
Figure 9G:
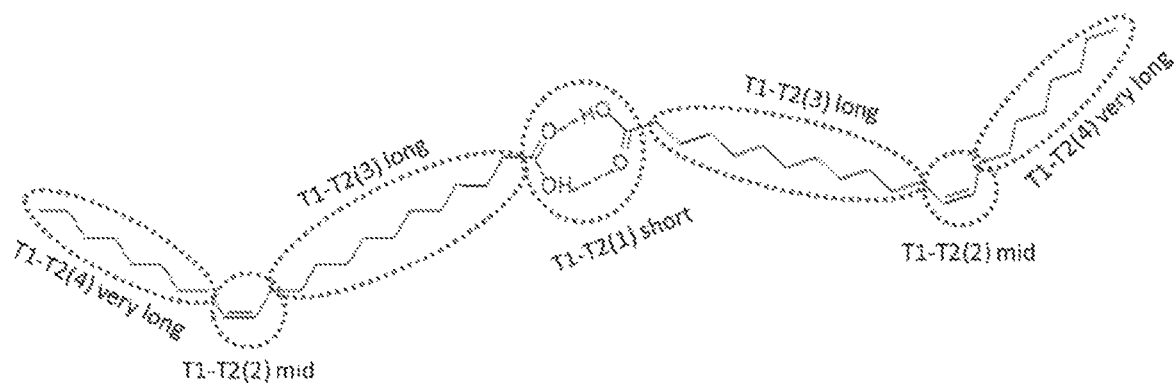

The comparison between the original simulated 2D spectrums and their corresponding reconstruction is shown in FIGS. 8A-8B (corresponding to the case where all three peaks are located in the diagonal). It is evident that PDCO retrieves the peak locations with great accuracy.

The simulation of the reconstructed spectrum generated by the LF H1 NMR signal analysis system is useful approach to confirm the validity of aforementioned signal analysis in the present invention. The simulation may be used as a quality control analysis of the machine system analysis of generated 2D and 3D T1 vs. T2 signals. The simulation can be used to determine the signal to noise ratio that the machine analysis of the T1 T2 signals can tolerate without generating extra peaks or reducing the resolution of different sets of T1 vs T2 peaks.

Figure 10:
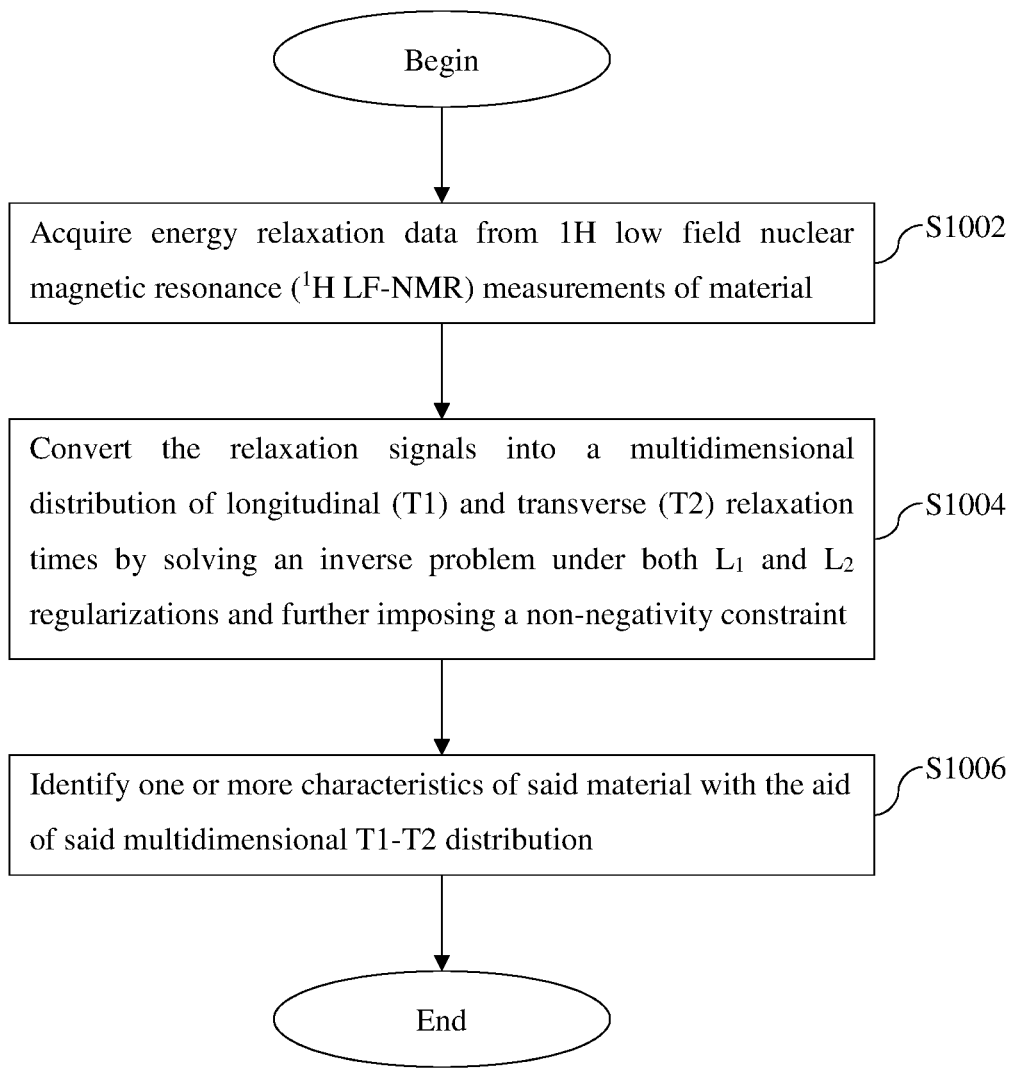
FIG. 10 is a flowchart showing method of characterizing chemical and/or morphological features of a material in accordance with certain example embodiments.

FIG. 10 is a flowchart showing method of characterizing chemical and/or morphological features of a material in accordance with certain example embodiments. As shown in FIG. 10, in step S1002, energy relaxation data is acquired from 1H low field nuclear magnetic resonance ($^1$H LF-NMR) measurements of said material. In step S1004, the relaxation signals are converted into a multidimensional distribution of longitudinal (T1) and transverse (T2) relaxation times by solving an inverse problem under both $L_1$ and $L_2$ regularizations and further imposing a non-negativity constraint. In step S1006, one or more characteristics of said material is/are identified with the aid of said multidimensional T1-T2 distribution.

The invention claimed is:

1. A method of characterizing chemical and/or morphological features of a material, the method comprising:
   acquiring energy relaxation data from 1H low field nuclear magnetic resonance ($^1$H LF-NMR) measurements of said material in an NMR system,
   converting, via machine analysis, the relaxation data into a multidimensional distribution of longitudinal (T1) and transverse (T2) relaxation times by solving an inverse problem under both $L_1$ and $L_2$ regularizations and further imposing a non-negativity constraint, and
   identifying one or more characteristics of said material with the aid of said multidimensional T1-T2 distribution and the machine analysis.

2. A method according to claim 1, wherein the regularization parameters $\lambda_1$ and $\lambda_2$ that are assigned to the $L_1$ and $L_2$ norms, respectively, are set according to a signal-to-noise level of the measurements, signal intensity, dimensions of the acquired energy relaxation data and dimensions of an input matrix of distribution components.

3. A method according to claim 1, further comprising:
   i) acquiring relaxation data from $^1$H LF-NMR measurements;
   ii) computing multidimensional T1-T2 spectrum by solving the following minimization problem:

$$\min_{f,c,r} \lambda_1 \|c\|_1 + \frac{1}{2}\lambda_2\|c\|_2^2 + \frac{1}{2}\|r\|_2^2 \quad (1)$$

$$\text{s.t. } K_1 F K_2 + R = S,$$

$$-f + Bc = 0, \ f \geq 0,$$

wherein:
S is $ns_1 \times ns_2$ matrix with the measured relaxation data;
F is $nf_1 \times nf_2$ matrix of unknown distribution components, and f=vec(F) is a vector with length of $nf_1 \times nf_2$ containing the elements of the matrix F concatenated by columns;
$K_1$ and $K_2$ and are Laplace operators which are matrices of sizes ns1×nf1 and ns2×nf2, respectively, and their elements are defined as follows:

$$K_1(i,j) = 1 - 2\exp\left(-\frac{t_1(i)}{T_1(j)}\right), i=1,\ldots,ns_1 \ j=1,\ldots,nf_1$$

$$K_2(i,j) = \exp\left(-\frac{t_2(i)}{T_2(j)}\right), i=1,\ldots,nf_2 \ j=1,\ldots,ns_2$$

R is a matrix of residuals, and r=vec(R) is a vector of the elements of the matrix R concatenated by columns;
B is a dictionary matrix,
c is a representation of the solution f by the B dictionary, and wherein the problem is solved with a penalty function comprising $L_1$ regularization term $\lambda_1\|c\|_1$ and $L_2$ regularization term $\lambda_2\|c\|_2^2$, where $\lambda_1$ and $\lambda_2$ are the $L_1$ and $L_2$ regularization parameters, respectively, and further with a non-negativity constraint imposed on the solution;
iii) displaying said spectrum in the form of a multidimensional map having at least T1 relaxation axis and T2 relaxation axis; and
iv) assigning one or more peaks identified in said spectrum to a chemical and morphological feature of said material.

4. A method according to claim 3, wherein $\lambda_1$ and $\lambda_2$ are calculated by the formulas:

$$\lambda_1 = C_1 \times SMX \times \frac{ns_1 \times ns_2}{nf_1 \times nf_2 \times SNR}$$

$$\lambda_2 = C_2 \times SMX \times \frac{ns_1^2 \times ns_2^2}{nf_1^2 \times nf_2^2 \times SNR}$$

wherein:
$C_1$ is from 0.1 to 0.5;
$C_2$ is from 0.0003 to 0.0007;
SMX is the maximal magnitude of the relaxation signal array after light smoothing; and
SNR is the signal to noise ratio of the measured relaxation coefficients.

5. A method according to claim 1, further comprising computing a multidimensional T1-T2 spectrum and quantifying peaks in the spectrum.

6. A method according to claim 1, wherein the material to be characterized is selected from the group consisting of fatty acids and fatty acid esters.

7. A method according to claim 1, wherein the material to be characterized is a complex material consisting of a mixture of individual substances, a mixture distinct phases or a mixture of distinct morphological domains.

8. A method according to claim 7, wherein the material is selected from the group consisting of vegetable oils, animal oils and biodiesel.

9. A method according to claim 7, wherein the material to be characterized is in the form of emulsion.

10. A method according to claim 7, wherein the material to be characterized is a plant seed.

11. A method for monitoring a process involving a starting material undergoing a chemical and/or a morphological change upon conversion to an end product, the method comprising:
   acquiring relaxation data from $^1$H LF-NMR measurements in an NMR system;
   generating at least one T1-T2 multidimensional spectrum, either for the starting material and/or for a progressively formed reaction mass;
   measuring via machine analysis one or more peaks in said spectrum or spectra, wherein said peak is associated with a process variable;
   using the process variable to monitor the process; and
   optionally modifying said process variable.

12. A method according to claim 11, wherein T1-T2 multidimensional spectrum/spectra is/are generated by the solving the following minimization problem:

$$\min_{f,c,r} \lambda_1 \|c\|_1 + \frac{1}{2}\lambda_2\|c\|_2^2 + \frac{1}{2}\|r\|_2^2 \quad (1)$$

-continued $$\text{s.t. } K_1 F K_2 + R = S,$$

$$-f + Bc = 0, f \geq 0,$$

wherein:
S is $ns_1 \times ns_2$ matrix with the measured relaxation data;
F is $nf_1 \times nf_2$ matrix of unknown distribution components, and f=vec(F) is a vector with length of $nf_1 \times nf_2$ containing the elements of the matrix F concatenated by columns;
$K_1$ and $K_2$ and are Laplace operators which are matrices of sizes ns1×nf1 and ns2×nf2, respectively, and their elements are defined as follows:

$$K_1(i, j) = 1 - 2\exp\left(-\frac{t_1(i)}{T_1(j)}\right), i = 1, \ldots, ns_1 \; j = 1, \ldots, nf_1$$

$$K_2(i, j) = \exp\left(-\frac{t_2(i)}{T_2(j)}\right), i = 1, \ldots, nf_2 \; j = 1, \ldots, ns_2$$

R is a matrix of residuals, and r=vec(R) is a vector of the elements of the matrix R concatenated by columns;
B is a dictionary matrix,
c is a representation of the solution f by the B dictionary, and wherein the problem is solved with a penalty function comprising $L_1$ regularization term $\lambda_1 \|c\|_1$ and $L_2$ regularization term $\lambda_2 \|c\|_2^2$, where $\lambda_1$ and $\lambda_2$ are the $L_1$ and $L_2$ regularization parameters, respectively, and further with a non-negativity constraint imposed on the solution.

13. A method according to claim 11, wherein the process variable is used to predict conversion yield of the starting material or track the progress of the process.

14. A method according to claim 11, wherein the process variable is modified by adjusting the composition of the starting material or intermediate materials to enhance rate of conversion.

15. A method according to claim 11, wherein the process monitored is the anaerobic digestion of a biomass.

16. A method according to claim 15, wherein the process variable used for monitoring the process is the amorphous cellulose content of the biomass.

17. A method according to claim 11, wherein the process monitored is biodiesel production.

18. A method for screening chemical additives to determine their ability to inhibit a chemical reaction that a substance of interest is susceptible to undergoing or advance a chemical reaction that a substance of interest is considered as a candidate for, the method comprising:
exposing a mixture consisting of the substance and a tested additive to conditions of the chemical reaction under consideration;
acquiring relaxation data from $^1$H LF-NMR measurements in an NMR system;
generating a T1-T2 map for said mixture;
comparing, via machine analysis, one or more spectral features exhibited by the generated T1-T2 map with corresponding spectral features observed either in a first reference T1-T2 map of the intact substance, a second reference T1-T2 map of the substance when exposed in the absence of the said additive to the conditions of the chemical reaction under consideration, or with both reference maps; wherein increased similarity between the generated T1-T2 map and the first reference map indicates that the tested additive is a useful stabilizer, whereas increased similarity between the generated T1-T2 map and the second reference map indicates that the tested additive promotes, or at least does not interfere with, the reaction under consideration.

19. A method according to claim 18, wherein the map is generated by solving the following minimization problem:

$$\min_{f,c,r} \lambda_1 \|c\|_1 + \frac{1}{2}\lambda_2 \|c\|_2^2 + \frac{1}{2}\|r\|_2^2 \quad (1)$$

$$\text{s.t. } K_1 F K_2 + R = S,$$

$$-f + Bc = 0, f \geq 0,$$

wherein:
S is $ns_1 \times ns_2$ matrix with the measured relaxation data;
F is $nf_1 \times nf_2$ matrix of unknown distribution components, and f=vec(F) is a vector with length of $nf_1 \times nf_2$ containing the elements of the matrix F concatenated by columns;
$K_1$ and $K_2$ and are Laplace operators which are matrices of sizes ns1×nf1 and ns2×nf2, respectively, and their elements are defined as follows:

$$K_1(i, j) = 1 - 2\exp\left(-\frac{t_1(i)}{T_1(j)}\right), i = 1, \ldots, ns_1 \; j = 1, \ldots, nf_1$$

$$K_2(i, j) = \exp\left(-\frac{t_2(i)}{T_2(j)}\right), i = 1, \ldots, nf_2 \; j = 1, \ldots, ns_2$$

R is a matrix of residuals, and r=vec(R) is a vector of the elements of the matrix R concatenated by columns;
B is a dictionary matrix,
c is a representation of the solution f by the B dictionary, and wherein the problem is solved with a penalty function comprising $L_1$ regularization term $\lambda_1 \|c\|_1$ and $L_2$ regularization term $\lambda_2 \|c\|_2^2$, where $\lambda_1$ and $\lambda_2$ are the $L_1$ and $L_2$ regularization parameters, respectively, and further with a non-negativity constraint imposed on the solution.

20. A method according to claim 18, wherein stabilizers are screened to determine their ability to minimize degradation reaction of a substance.

21. A method according to claim 20, wherein the stabilizers are antioxidants.

22. A method of monitoring quality of a product to enter a process or to result from a process, said method comprising:
acquiring energy relaxation data of said product using LF-NMR in an NMR system;
generating at least one T1-T2 multidimensional spectrum;
identifying one or more characteristics of said product within said multidimensional T1-T2 distribution,
comparing said one or more characteristics of T1-T2 distribution with respective characteristics obtained from a product of known quality via machine analysis; and
based on the comparison and the machine analysis, making a decision whether the product should be approved, rejected, or modified by addition of a stabilizer.

23. A method according to claim 22, wherein T1-T2 multidimensional spectrum/spectra is/are generated by the solving the following minimization problem:

$$\min_{f,c,r} \lambda_1 \|c\|_1 + \frac{1}{2}\lambda_2 \|c\|_2^2 + \frac{1}{2}\|r\|_2^2 \quad (1)$$

$$\text{s.t. } K_1 F K_2 + R = S,$$

$$-f + Bc = 0, f \geq 0,$$

wherein:

S is $ns_1 \times ns_2$ matrix with the measured relaxation data;

F is $nf_1 \times nf_2$ matrix of unknown distribution components, and f=vec(F) is a vector with length of $nf_1 \times nf_2$ containing the elements of the matrix F concatenated by columns;

$K_1$ and $K_2$ and are Laplace operators which are matrices of sizes ns1×nf1 and ns2×nf2, respectively, and their elements are defined as follows:

$$K_1(i,j) = 1 - 2\exp\left(-\frac{t_1(i)}{T_1(j)}\right), i = 1, \ldots, ns_1 \; j = 1, \ldots, nf_1$$

$$K_2(i,j) = \exp\left(-\frac{t_2(i)}{T_2(j)}\right), i = 1, \ldots, nf_2 \; j = 1, \ldots, ns_2$$

R is a matrix of residuals, and r=vec(R) is a vector of the elements of the matrix R concatenated by columns;

B is a dictionary matrix, c is a representation of the solution f by the B dictionary, and wherein the problem is solved with a penalty function comprising $L_1$ regularization term $\lambda_1 \|c\|_1$ and $L_2$ regularization term $\lambda_2 \|c\|_2^2$, where $\lambda_1$ and $\lambda_2$ are the $L_1$ and $L_2$ regularization parameters, respectively, and further with a non-negativity constraint imposed on the solution.

24. A method according to claim 23, wherein the product is selected from the group consisting of food products, a fuel product, a pharmaceutically active compound, a pharmaceutical preparation and a cosmetic.

25. A method according to claim 24, wherein the product is selected from the group consisting of a fatty acid, an oil, mayonnaise, nutritional seeds, and bovine cream butter.

26. A method according to claim 24, wherein the product is a biodiesel product selected from the group consisting of fatty acid derivatives.

\* \* \* \* \*